United States Patent
Sakayori

(10) Patent No.: US 7,528,205 B2
(45) Date of Patent: May 5, 2009

(54) PHOTO RADICAL GENERATOR, PHOTO SENSITIVE RESIN COMPOSITION AND ARTICLE

(75) Inventor: Katsuya Sakayori, Tokyo (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 0 days.

(21) Appl. No.: 10/945,697

(22) Filed: Sep. 21, 2004

(65) Prior Publication Data

US 2005/0119432 A1    Jun. 2, 2005

(30) Foreign Application Priority Data

Sep. 26, 2003   (JP)   ............... 2003-336436
Mar. 30, 2004   (JP)   ............... 2004-101325

(51) Int. Cl.
 C08F 2/48   (2006.01)
 C08F 2/46   (2006.01)

(52) U.S. Cl. ............ 526/348; 526/217; 528/322; 528/228; 430/326

(58) Field of Classification Search ............ 526/266, 526/280, 217, 348; 522/26, 48, 174; 428/473.5; 528/322, 228; 430/326
See application file for complete search history.

(56) References Cited

U.S. PATENT DOCUMENTS

| | | | | |
|---|---|---|---|---|
| 4,739,034 A | * | 4/1988 | Lindley | ............ 528/322 |
| 4,808,695 A | * | 2/1989 | Jones | ............ 528/322 |
| 5,002,853 A | * | 3/1991 | Aoai et al. | ............ 430/270.1 |

FOREIGN PATENT DOCUMENTS

| | | | |
|---|---|---|---|
| JP | 63 187247 | * | 8/1988 |
| JP | 02 093470 | * | 4/1990 |
| JP | 2002003559 | | 1/2002 |
| JP | 2004149759 | | 5/2004 |

| | | |
|---|---|---|
| WO | WO98/58912 | 12/1998 |

OTHER PUBLICATIONS

Ruediger et al. Can. J. Chem., 64, 577-579(1986).*
Goins et al., Polymer Letters, 6, 821-825(1968).*
Barton et al., J. Chem. Soc. (C), 729-736(1971).*
Kubo et al., Bull. Chem. Soc. Jpn., 58, 2863-2869(1985).*
Jones et al., Polymer, 29, 1699-1703(1988).*
"Radical Polymerization Handbook"; (NTS Co. Ltd., 1999, p. 312).
Yasuo Kubo et al; "Photoreactions of N-Methyl-1,8-naphthalimide with Methylbenzenes: (3+3)-Additions and Water-Incorporated Additions" Chemistry Letters 1999.

* cited by examiner

*Primary Examiner*—Ling-Siu Choi
(74) *Attorney, Agent, or Firm*—Ladas & Parry LLP

(57) ABSTRACT

A photoradical generator which produces no low-molecular decomposition material but a radical during a photoradical generating process, does not generate a radical during a heating process, exists in a chemically stable state in a resulting product of a radical reaction such as a cured coating layer or the like, has high heat resistance, stability and preserving ability, and is excellent in compatibility or solubility is provided. The photoradical generator is comprised of a compound (a) having a seven-membered ring imide structure-containing group represented by the following formula (1), wherein, $R^1$ to $R^8$ respectively represent a hydrogen atom or a substituent and may be a cyclic structure in which they are bonded to each other.

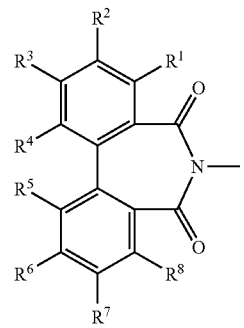

Formula (1)

11 Claims, 4 Drawing Sheets

F I G. 1
A seven-membered ring imide viewed from above the aromatic rings
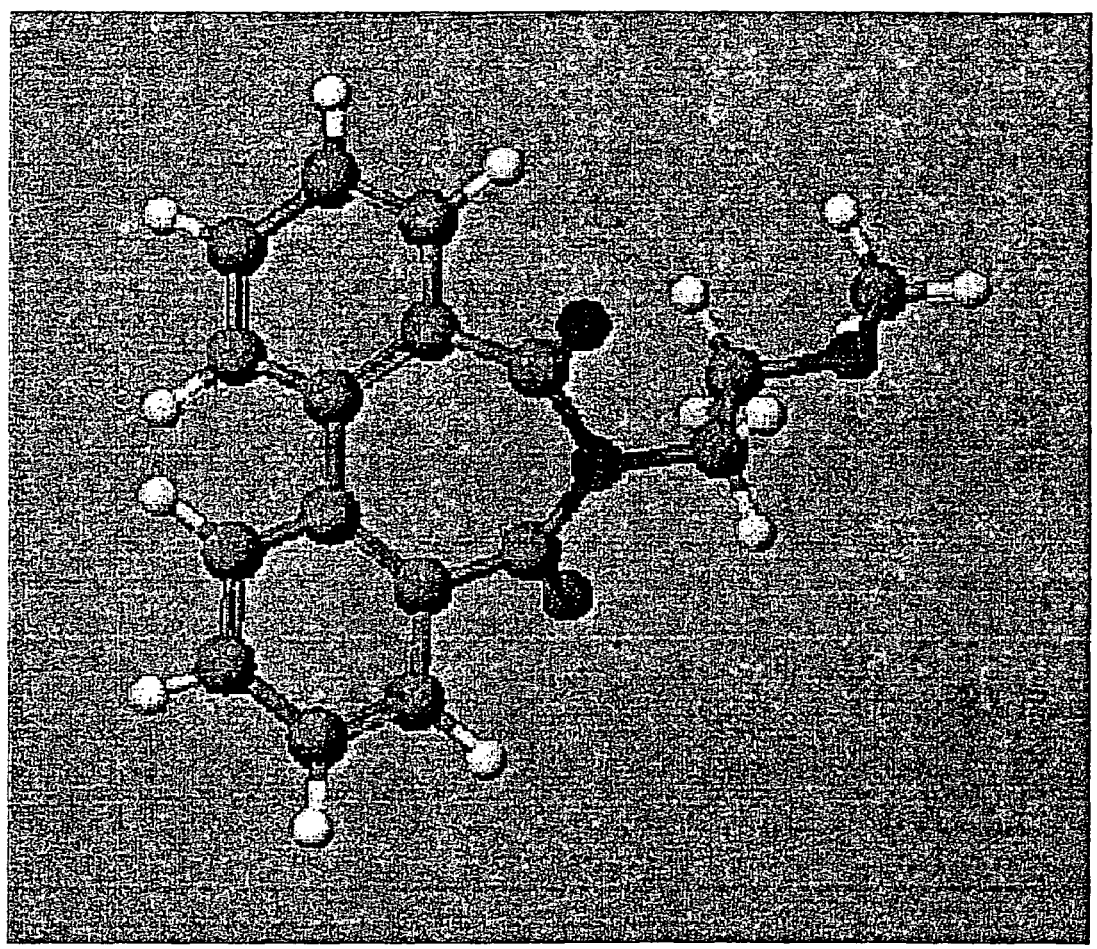

A seven-membered ring imide viewed from the direction of an ax which bonds the aromatic rings An ultraviolet absorption spectrum of the compounds 1 and 15 (an acetonitrile solution containing $1.0 \times 10^{-5}$ mol/L of each of the compounds)

A transmittance of each of the compound 1, the compound 1 + triethanol amine and Irg907 (a tetrahydrofuran solution)

PHOTO RADICAL GENERATOR, PHOTO SENSITIVE RESIN COMPOSITION AND ARTICLE

BACKGROUND OF THE INVENTION

1. Field of the Invention

The present invention relates to utilization of a compound having a seven-membered ring imide structure as a photoradical generator, a photosensitive resin composition containing the photoradical generator and a product produced using the photosensitive resin composition.

The invention relates, particularly, to a photoradical generator which has high heat resistance and stability, is excellent in compatibility with other components such as of a monomer or the like and solubility to a solvent, is high in transparency, and remains little decomposition material of low molecular weight and unstable unreacted substance after a radical reaction. Also, the invention relates to a photosensitive resin composition which contains the photoradical generator, is high in sensitivity, is excellent in storage stability and is less liable to emit a volatile component and a odor upon light radiation resulting from an initiator, and further relates to an article at least a part of which is formed of the photosensitive resin composition, and which has little low molecular or unstable residue derived from an initiator remained, and has high heat resistance, stability and quality.

2. Description of the Related Art

Photosensitive resins which are cured or changed in solubility by irradiation of radial rays such as ultraviolet rays are generally classified into two categories including a type (positive type) in which an exposed portion is highly soluble and a type (negative type) in which an unexposed portion is highly soluble. In the case of the negative type, the photosensitive resin remains on a substrate and often becomes a part of a product as a functional layer because the photosensitive resin itself is cured and becomes insoluble by exposure.

Although the negative type photosensitive resin has been used for, for example, paints, printing inks, overcoat layers, adhesives, printing master plates or the like, it has been recently used in wide applications ranging to products such as solder resists for wire protection in printed wiring boards, layer insulation films and resists for forming pixels in color filters, antireflection films, hologram or the like.

As one of the negative type photosensitive resins which are frequently used in general, there are resin compositions containing a compound having one or more ethylenic unsaturated bonds, a photoradical initiator generating a radical by irradiation with light and, as required, a high molecular compound providing developing ability, softness to a coating layer or the like, an inorganic filler, pigments or the like. When radial rays are applied to this composition, the compounds having an ethylenic unsaturated bond are bonded to each other by a radical reaction and cured as a macromolecule. In this curing reaction, a three-dimensional network structure is developed by a crosslinking reaction, improving the hardness, strength, adhesiveness, resistance to solvent and heat resistance of the resulting cured product.

The photoradical initiators are roughly classified into a self cleavage type and a hydrogen-drawing type. In the case of the former type, it absorbs light (radial rays) having a specific wavelength, the bond at a part corresponding to that wavelength is cut, radicals are generated in each part cut at this time and a radical reaction starts from these parts. In the case of the latter type, when it absorbs a radial ray having a specific wave length and put into an excited state, it draws hydrogen from surrounding hydrogen donors. At this time, radicals are generated from each of the drawing one and the drawn one.

Generally, the self-cleavage type has good sensitivity and high radical-generating efficiency, but is unstable to heat, giving rise to the problems concerning the heat resistance, stability and preserving stability of a photosensitive resin composition containing this self-cleavage type. In the case of the hydrogen-drawing type, on the other hand, the hydrogen donor must exist in the vicinity of the excited initiator and the radical-generating efficiency is decided by the magnitude of an energy barrier when drawing hydrogen. Therefore, this type has relatively low sensitivity, but a resin composition containing this type exhibits high stability and preserving stability because no radical is generated unless it is put in an excited state and draws hydrogen.

In the solder resist used for surface coating in a print board, an organic pigment and filler are compounded to provide heat resistance and flame resistance. Also, in a resist used for forming pixels of a color filter, a pigment for color indication is compounded. Because these pigments are components absorbing light, a self-cleavage type photoradical initiator is principally used to raise the sensitivity of a photosensitive resin and also the photoradical initiator is compounded in a large amount allowing for a portion which will not fully used in a radical reaction. Here, the portion which is not fully used in a radical reaction includes an unreacted initiator which has not been cleft even by irradiation with light and an initiator whose activity is lost by prohibiting its access to material to be caused reaction because of a reaction in a solid phase even if it is radicalized by cleavage.

A large amount of residues originated from an initiator exists in the cured product after exposure. Among these residues, a photoradical initiator which has not been cleft still keeps reactivity even after exposure and therefore denatures a product. Also, a photoradical initiator which has not been cleft and a decomposed material which has been cleft but not consumed in a radical reaction and deactivated is not bonded to a crosslinking structure of a matrix and exists as an independent component in a product, which impairs the quality of a layer. For this, if a residue originated from an initiator is left as it is, there is a problem that it causes deteriorated light resistance, coloring, fading, peeling of a coating layer, the occurrence of cracks or the like, which is a cause of a reduction in the reliability of a final product such as a layer insulation film and solder resist in electronic parts and a resist used for forming pixels in a color filter.

The self-cleavage type photoradical initiator has a strong sublimation tendency and is decomposed by heat. It can be therefore removed from a product by post-baking after exposure and developing at a temperature higher than hundred and several tens degree. However, a large amount of a sublimated material originated from an initiator adheres to the inside of a heater and falls on a product obtained by curing during post-baking, causing product defects, posing a serious problem. Also, a decomposed material of an initiator or the like is involved in the atmosphere around the heater, posing a problem from the viewpoint of operational safety.

It is possible to remove more residues originated from a radical initiator by changing a post-baking condition to a condition of a higher-temperature and longer-operation time. However, it is difficult to remove the residues completely because of volatilization from a solid. If the condition is made stricter to remove many more impurities originated from a radical initiator, this condition rather causes product defects.

In the meantime, the same curing system using radial rays is applied to a resist for processing electronic parts to be used as a peelable layer and a dry film resist or the like. The processing resist is finally peeled off and is not therefore left in a product. However, the processing step such as formation of copper wirings or the like involves such a problem that a residue originated from an initiator is eluted in a chemical solution such as ferric chloride and cupric chloride used for the processing from a resist film, so that the life of the chemical solution is shortened.

Moreover, when a photosensitive resin is used as a wall used for buildings or paint for a protective layer protecting a surface of wall paper, there is a demand for decreasing solvent components or odorous components emitting from whole building material with the view of dealing with sick house syndrome. There is a problem that the use of a highly volatile initiator causes the occurrence of odors even after curing.

From these problems, it has been desired to develop a radical generator and a resin composition which are not volatilized during post-baking and after photo-curing and are substantially free of components which are originated from a radical generator and remain independently in a coating layer.

As measures to solve these problems, ESACURE KIP 150 (trademark, manufactured by Nihon Siber Hegner CO., LTD.) or the like introduces a photoradical-generating part into the side chain of a polymer skeleton. This measure ensures that a photoradical generator has plural radical-generating parts in one molecule. Therefore, if any one part in the molecule is radicalized and bonded to a matrix of the coating layer, an unreacted radical-generating part in the same molecule is bonded to the matrix through the polymer skeleton. For this, the photoradical generator is not volatilized during post-baking and does not move in the coating layer, and deterioration of the reliability of a final product is a little.

In this case, however, the photoradical-generating part introduced into the side chain is a self-cleavage type and is easily decomposed by heating to produce a radical, still posing the same problems concerning, for example, the heat resistance, stability and preserving ability of a photosensitive resin composition containing this product. Although, among the radical-generating parts, the part left on the polymer skeleton after cleavage is bonded to the matrix structure, a part of the decomposed material cleft from the polymer skeleton by a photoradical reaction and post-baking remains independently not bonded to the matrix structure. Therefore, if the decomposed material is left as it is, it adversely affects the physical properties of a coating layer, and it is also difficult to remove the decomposed material perfectly by sublimation even if post-baking is carried out.

There is a proposal as to the use of (meth)acrylates having a maleimide group in each publication of International Publication No. WO98/58912 and Japanese Patent Application Laid-Open No. 2002-3559. These (meth)acrylates react with vinyl ether to generate a radical as an electron acceptor because maleimide absorbs electromagnetic waves. Also, these (meth)acrylates draw hydrogen, whereby a radical can also be generated (RADICAL POLYMERIZATION HANDBOOK, NTS Co., Ltd., 1999, page 312). However, maleimide has an ethylenic double bond. If a monomer having both maleimide group and (meth)acryl group is radical-polymerized, a crosslinking reaction proceeds and the resulting polymer is gelled. For this, according to each publication of International Publication No. WO98/58912 and Japanese Patent Application Laid-Open No. 2002-3559, a substituent such as a cyclohexyl group is introduced into a maleimide group to lower the reactivity of the maleimide group by steric hindrance, whereby the above problem is overcome. However, since the reactivity of the maleimide is lowered on the contrary, there is the problem that the efficiency of initiation of a radical reaction is dropped. Also, because the reaction for forming a maleimide group by reacting an acid anhydride with an amine is carried out by a dehydration reaction, a temperature as high as 100° C. or more is required to react highly efficiently without using a catalyst. If it is intended to introduce an ethylenic unsaturated bond directly when forming the maleimide group, there is a synthesis problem that polymerization of the ethylenic unsaturated bond is caused. Also, although a dehydrating catalyst such as acetic acid anhydride or the like may be used to carry out a dehydration reaction. However, this causes a cost increase and also the subsequent refining process is complicated, giving rise to a synthesis problem in any case.

In the meantime, Kubo et al. report that when N-methyl-1, 8-naphthalimide and an aromatic compound such as p-xylene or the like are irradiated with ultraviolet rays in the presence of methanol in an acetonitrile solution, a reaction product of naphthalimide and the aromatic compound is obtained in a high yield (Chemistry Letters, 1999, page 175). There is the description in this report that as its reaction mechanism, naphthalimide which is singlet-excited by ultraviolet rays forms an exciplex with the aromatic compound and then the exciplex generates a radical by drawing hydrogen to form a bond between the naphthalimide and the aromatic compound. However, in this document, there is only a description of a reaction in a solution between naphthalimide and low molecular aromatic compounds in a partial scope.

In light of the aforementioned knowledge, the inventors of the present invention proposed a photoradical polymerization initiator having a group(s) containing naphthalimide structure which is a six-membered ring structure imide group, and a radial sensitive resin composition (Japanese Patent Application No. 2003-88582). The naphthalimide containing group functions as a hydrogen-drawing type photoradical generating part, hence, the naphthalimide does not decompose but generates radical in a photoradical generating process, and does not generate radical in a general heating process. The naphthalimide structure itself has high heat resistance. Also, the naphthalimide structure can be synthesized in a relatively moderate condition. Therefore, a photoradical polymerization having a group containing a naphthalimide structure has high heat resistance, and low-molecular decomposition materials or unreacted products do not remain in a product (particularly, a coating layer after curing) after a radical reaction. Further, the photoradical polymerization initiator having a group containing a naphthalimide structure can be relatively easily produced.

However, the photoradical polymerization initiator having a group containing a naphthalimide structure has not so high compatibility with acrylic polyfunctional monomer generally used for a negative type photosensitive resin composition or solubility to general solvent, thus, there has been a problem that the photoradical polymerization initiator deposits when contained in high concentration in a photosensitive resin composition.

SUMMARY OF THE INVENTION

An object of the present invention is to provide a novel hydrogen-drawing type photoradical generator improved in compatibility or solubility which has been problems to a photoradical generator having a group containing the aforementioned naphthalimide structure and a photosensitive resin composition using the photoradical generator, further an article at least a part of which is formed by using the photosensitive resin composition.

Specifically, a first object of the present invention is, similarly to a photoradical generator having a group containing a naphthalimide structure, to provide a hydrogen-drawing type photoradical generator which produces no low-molecular decomposition material but a radical during a photoradical generating process, does not generate a radical during a heating process, exists in a chemically stable state in a solution of a resulting product such as a cured coating layer or the like, and has high heat resistance, stability and preserving ability.

A second object of the present invention is to provide a photosensitive resin composition which uses the aforementioned photoradical generator according to the present invention, does not produce a low-molecular decomposition material derived from an initiator after radical polymerization, has high sensitivity to practical wavelength, does not produce volatile components or emit foul odor upon light radiation, has high sensitivity to a practical wavelength, and possesses high stability and preserving ability.

A third object of the present invention is to provide a product at least a part of which is formed of a cured product of the photosensitive resin composition according to the present invention and which remains low-molecular or unstable residue derived from an initiator, and has high heat resistance, stability and quality.

The present invention is to solve at least one of these objects.

In order to solve the above problem, a photoradical generator of the present invention is comprised of a compound (a) having a seven-membered ring imide structure-containing group represented by the following formula (1):

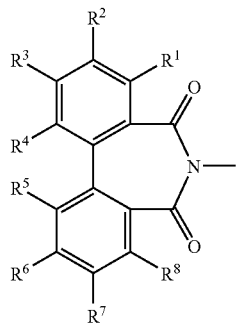

Formula (1)

wherein, $R^1$, $R^2$, $R^3$, $R^4$, $R^5 R^6$, $R^7$ and $R^8$ respectively represent a hydrogen atom or a substituent and may be a cyclic structure in which they are bonded to each other.

A photoradical initiator of the present invention can be suitably used as a photoradical polymerization initiator since the seven-membered ring imide structure-containing group of the compound (a) functions as a hydrogen-drawing type radical-generating part.

As a radical generated by the seven-membered ring imide structure-containing group goes through of a hydrogen-drawing mechanism, the radical can not only react with a general radical polymerizable group such as an ethylenic unsaturated bond or the like but also with various compounds such as an aromatic ring or the like. Hence, the compound (a) can not only be used as a general photoradical polymerization initiator but also as various initiators or promoters of radical reaction. For example, the compound (a) can be used as a crosslinking agent of a resin composition containing a low-molecular weight aromatic compound or an aromatic polymer.

The seven-membered ring imide structure-containing group generates a radical by light radiation, but does not generate radical by heating of a temperature in practical range. The seven-membered ring imide structure-containing group of a photoradical generator of the present invention is highly stable and less likely to cause heat decomposition similarly to a six-membered ring imide structure. Hence, a photoradical generator of the present invention has high heat resistance, stability and preserving ability due to a radical generating mechanism and further due to a chemical structure of a radical generating part. A photoradical generator of the present invention has almost equal heat resistance as a compound having a six-membered naphthalimide structure-containing group.

A photoradical generator of the present invention is superior to the compound having a six-membered naphthalimide structure-containing group particularly in compatibility and solubility, and has more freedom of mixing ratio with other component such as polyfunctional monomer, acrylic resin or the like than the compound having a six-membered naphthalimide structure-containing group. Also, a photoradical generator of the present invention is superior to the compound having a six-membered naphthalimide structure-containing group in transparency. A photoradical generator of the present invention is excellent in sensitivity besides having high transparency.

Also, a photoradical generator comprising the compound (a) is a hydrogen-drawing type. Thus, different from the case using a self-cleavage type (Type I), it is not necessary to volatilize the compound during post-baking since low-molecular decomposition materials do not remain after a radical reaction. Furthermore, even if an unreactant of the compound (a) remains, the compound (a) exists in a stable state.

Therefore, various problems caused by decomposition materials or unreactants after reaction derived from a photoradical initiator, for example, a problem concerning operational safety, problems concerning a decline in the reliability of a final product such as deteriorated heat resistance or light resistance, coloring, fading and peeling and cracks of a coating layer, a problem as to short life of a chemical solution and a problem concerning the generation of an odor (outgas) can be all solved.

Next, a photosensitive resin composition of the present invention is comprised of a compound (a) having a seven-membered ring imide structure-containing group represented by the formula (1) and a compound (b) having an ethylenic unsaturated group.

A resin composition of the present invention contains a photoradical generator comprising a compound (a), as an initiator, which is high in heat resistance and quite high in solubility and compatibility with solvents and other compounded components, hence, heat resistance, stability and preserving ability are high in the state of a resin composition.

In the case of forming a pattern or a molded body using the resin composition, there is no problem that a volatile low-molecular decomposition material or unstable unreactant derived from a radial initiator to remain in a cured product of the resin composition. As the result, there is an effect to raise heat resistance of cured product or layer or stability, thus, the problem concerning a decline in the reliability of a final product is solved. Also, since the generation of an odor (outgas) is not caused, a problem concerning operational safety improves.

Further, since a compound (a) has high sensitivity of temperature in a practical range besides high transparency, an effect of improved transparency of final product can be expected when the resin composition of the present invention is used.

When a photosensitive resin composition of the present invention is used as a pattern forming material, a paint or a printing ink, or as a material to form a color filter, electronic parts, a layer insulation film, a wire cover film, an optical member, an optical circuit, optical circuit parts, an antireflection film, a hologram or a building material, there is such an effect that the product or film has high heat resistance and high stability. Also, it is free from the generation of odors during exposure, which improves the operational circumstance.

As aforementioned, a photoradical generator of the present invention comprising a compound (a) having a seven-membered ring imide structure-containing group generate a radical by a hydrogen-drawing type radical mechanism to initiate or proceed various radical reactions such as a radical polymerization, a radical crosslinking reaction or the like, and does not leave a component causing problems such as a unstable unreactant or a volatile low-molecular decomposition material after reaction.

Moreover, a photoradical generator of the present invention has excellent compatibility or solubility which has been not sufficient conventionally besides almost equal heat resistance, stability and preserving ability as a compound having a six-membered ring structure imide group, which is a similar structure, and is high in transparency, thus, it serves many uses.

Heat resistance of a photosensitive resin composition of the present invention containing a photoradical generator comprising the compound (a) is equal to that of a compound having a six-membered structure imide group. Also, the photosensitive resin composition of the present invention contains a compound (a), as an initiator, which is quite high in solubility and compatibility with solvents or other compounded components. Therefore, the proportions of the compound (a), which is an initiator, can be freely adjusted to the wide range, and thus, it is useful. Further, the photosensitive resin composition of the present invention has high sensitivity, does not generate volatile components or odor during radical reaction, and has high quality or reliability of a final product. has excellent compatibility or solubility which has been not sufficient conventionally besides almost equal heat resistance, stability and preserving ability as a compound having a six-membered ring structure imide group, which is a similar structure, and is high in transparency, thus, it serves many uses.

A photosensitive resin composition of the present invention may be utilized in all known fields and products, using materials which are cured or changed in solubility by radiation with active energy ray, such as pattern-forming materials (resists), coating materials, printing inks, adhesives, fillers, molding materials and three-dimensional articles. Particularly, it is suitable for forming paints, printing inks, color filters, electronic parts, layer insulation films, wire cover films, optical members, optical circuits, optical circuit parts, antireflection films, holograms or building materials for which heat resistance is required and high reliability is demanded.

The printed product, color filter, electronic parts, layer insulation film, wire cover film, optical members, optical circuit, optical circuit parts, antireflection film, hologram or building material according to the present invention has such a merit that high heat resistance and stability of products and films are provided and therefore high product yield since at least a part thereof is formed of a cured product of the photosensitive resin composition having high heat resistance and stability.

BRIEF DESCRIPTION OF THE DRAWINGS

In the accompanying drawings,

FIG. 1 is a model showing the conformation of a compound having a seven-membered ring structure-containing group (a seven-membered ring imide viewed from above the aromatic rings);

DETAILED DESCRIPTION OF THE PREFERRED EMBODIMENT

Figure 2:
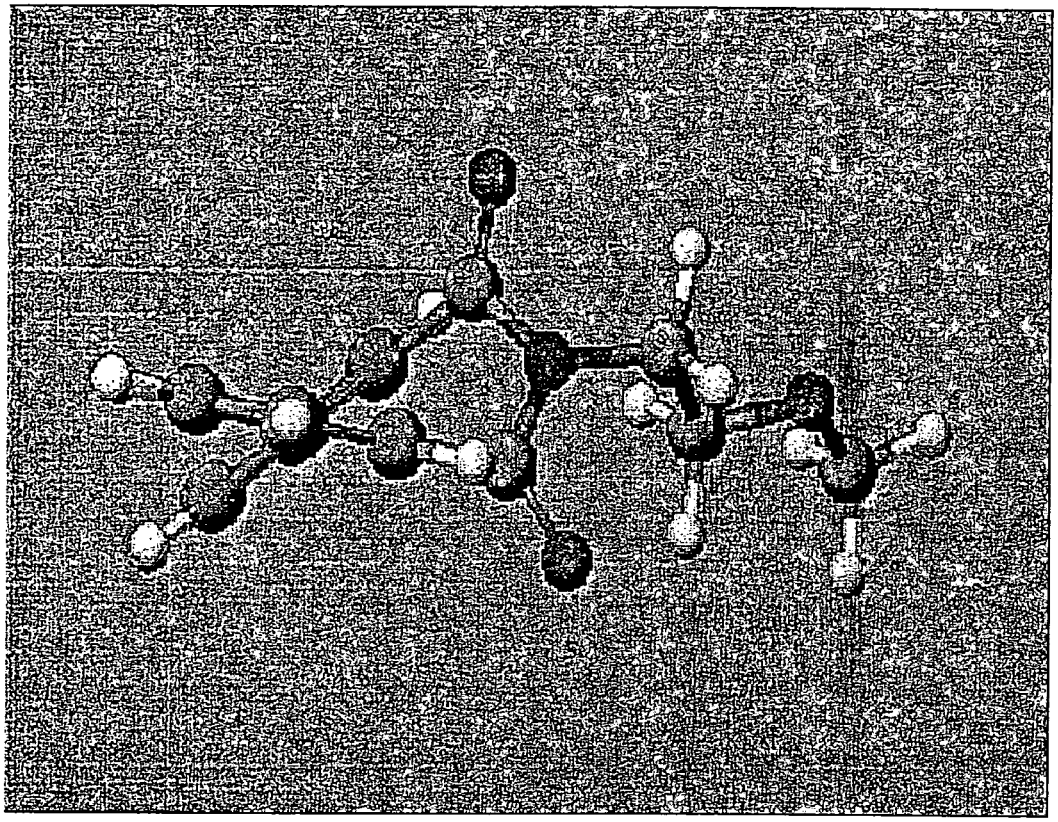
FIG. 2 is a model showing the conformation of a compound having a seven-membered ring structure-containing group (a seven-membered ring imide viewed from the direction of an ax which bonds the aromatic rings)

The present invention will be hereinafter explained in detail. In the present invention, the radiation light includes not only electromagnetic waves having wavelengths in the visible and invisible region and radicalizing the radical-generating part of a photoradical initiator or causing the photosensitive resin composition to enter into a radical reaction, but also corpuscular rays such as electron rays and radial rays which are a general term of electromagnetic waves and corpuscular rays or ionizing radial rays. Electromagnetic waves having a wavelength of 2 μm or less, electron rays, ionizing radial rays and the like are primarily used for the photo-curing of a resin composition.

First, a photoradical initiator according to the present invention will be explained. The photoradical initiator according to the present invention is comprised of a compound (a) having a seven-membered ring imide structure-containing group represented by the following formula (1):

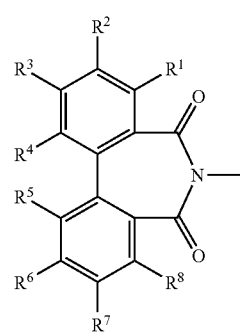

Formula (1)

wherein, $R^1$, $R^2$, $R^3$, $R^4$, $R^5$, $R^6$, $R^7$ and $R^8$ respectively represent a hydrogen atom or a substituent and may be a cyclic structure in which they are bonded to each other.

When the photoradical generator according to the present invention is radiated with light such as an electromagnetic wave, a corpuscular ray or the like, the above mentioned seven-membered ring imide structure-containing group can absorb light to be excited and generate a radical and can cause a radical reaction, initiate radical polymerization and crosslink polymers. In the photoradical generating process, it is inferred that the seven-membered ring imide structure-containing group functions as a hydrogen-drawing type radical-generating part as to the mechanism of generation of a radical.

The hydrogen-drawing type radical-generating part is not a part having a radical generating mechanism wherein a single bond cleaves to decompose a molecule and radicals of two molecules are generated to start polymerization such as the case of benzoin ether compounds but a part having a radical generating mechanism wherein a radical is generated without a decomposition of a molecular structure such as a mechanism represented by benzophenone. Generally, radical generators which belong to a radical generating mechanism wherein a single bond cleaves to decompose a molecule and radicals of two molecules are generated to start polymerization such as the case of benzoin ether compounds are classified as Type I and radical generators which belong to a hydrogen-drawing mechanism wherein a radical is generated without a decomposition of a molecular structure such as a mechanism represented by benzophenone (Photocurable technology, page 39, Technical Information Institute Co., Ltd., 2000). Thus, according to this classification, a photoradical generator of the present invention belongs to Type II.

In the seven-membered ring imide structure-containing group represented by the above formula (1), $R^1$, $R^2$, $R^3$, $R^4$, $R^5$, $R^6$, $R^7$ and $R^8$ in the formula are respectively a hydrogen atom or a substituent or may be a cyclic structure in which they are bonded to each other.

Examples of the substituent include a halogen atom, a hydroxyl group, a mercapto group, an amino group, a cyano group, a silyl group, a silanol group, an alkoxy group, a nitro group, a carboxyl group, an acetyl group, an acetoxy group, a sulfone group or a monovalent organic group which may have a substituent or may be a cyclic structure in which they are bonded to each other. Examples of the monovalent organic group which may have a substituent include a saturated or unsaturated alkyl group, saturated or unsaturated alkyl halide group or aromatic group such as a phenyl group, naphthyl group or the like, allyl group or the like. $R^1$ to $R^8$ may be same or different from each other.

When $R^1$ to $R^8$ are respectively a hydroxyl group or the aforementioned exemplified substituent, it is preferable from the viewpoint of easiness in the procurement of raw materials and synthetic simplicity.

Also, the term "substituents in a seven-membered ring imide structure-containing group may be a cyclic structure in which they are bonded to each other" means that not only aliphatic cyclic structures such as a cyclohexyl group or the like but also, for example, those having a naphthalene structure in which $R^6$ and $R^7$ are bonded or the like, and also those bonding to a seven-membered ring imide structure-containing group represented by the formula (1) via $R^1$, $R^2$, $R^3$, $R^4$, $R^5$, $R^6$, $R^7$ and $R^8$ to form a condensed cyclic hydrocarbon larger than the skeleton represented by the formula (1) as far as the imide ring has a seven-membered ring structure are included in the seven-membered ring imide structure-containing group according to the present invention. Also, the cyclic structure may be an aromatic condensed ring or an aliphatic cyclic structure and may further contain a heteroatom other than C as an atom composing the ring structure.

As the substituent introduced into the seven-membered ring imide structure-containing group of the compound (a), a saturated or unsaturated alkyl group having 1 to 15 carbon atoms, a saturated or unsaturated alkoxy group having 1 to 15 carbon atoms, a bromo group, a chloro group or a fluoro group, a nitro group, a primary to tertiary amino group or the like is preferable from the viewpoint of improving solubility when the photoradical generator is compounded in the photosensitive resin composition.

When the part to which N of the seven-membered ring imide structure-containing group is bonded is expressed as "X" in the above compound (a), the compound (a) may be represented by the following formula (2):

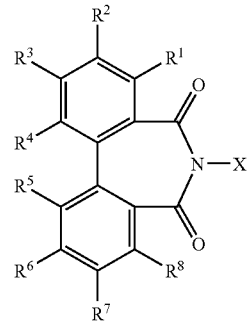

Formula (2)

wherein, $R^1$, $R^2$, $R^3$, $R^4$, $R^5$, $R^6$, $R^7$ and $R^8$ are as same as the formula (1); "X" is a monovalent chemical structure.

The chemical structure "X" contained in the formula (2) may be a monovalent one having any chemical structure and is typically an organic group. Examples of the organic group include hydrocarbon groups such as a straight-chain and/or branched and/or cyclic saturated or unsaturated alkyl group, aryl group, allyl group or the like. Further, one or more bonds such as a single bond, an ester bond, ether bond, thioether bond, amino bond, amide bond, urethane bond, urea bond, thiocarbamate bond, carbodiimide bond, carbonate bond or the like may be contained in these hydrocarbon groups.

In order to allow the seven-membered ring imide structure-containing group to fully exhibit a hydrogen-drawing ability, it is preferable that the chemical structure "X" has a non-aromatic skeleton a part of which is bonded to a nitrogen atom of the seven-membered ring imide structure-containing group. Herein, the term "non-aromatic skeleton" means an atom directly bonded to the nitrogen atom of the seven-membered ring imide structure-containing group is not a part of an aromatic ring. If this condition is meat, the chemical structure "X" may contain an aromatic structure.

Also, in view of improving the hydrogen-drawing ability of the seven-membered ring imide structure-containing group, it is preferable that an end portion of the chemical structure "X" further has a hydrogen-donating atom adjacent to the above-mentioned non-aromatic skeleton directly bonded to N of the seven-membered ring imide structure-containing group. When a hydrogen-donating atom exists near an end portion of the chemical structure "X" and the hydrogen-donating atom is bonded to N of the seven-membered ring imide structure-containing group via a non-aromatic skeleton which is an end portion of the chemical structure "X", hydrogen is transferred between the seven-membered ring imide structure-containing group and the hydrogen-donating atom of the chemical structure "X". Hence, it allows improvement in the hydrogen-drawing ability.

As the non-aromatic skeleton directly bonded to N of the seven-membered ring imide structure-containing group, there may be a hydrocarbon chain the straight skeleton portion of which has 1 to 20 carbons such as a methylene group and ethylene group. As the hydrogen-donating atom, there may be a methyl group or methylene group adjacent to the structure such as ether, amine, thioether or the like.

Specifically, there may be the structures represented by the following formulas. A methylene group with the mark "*1" in the formulas (3), (4) and (5) is an end portion having a non-aromatic skeleton structure directly bonded to N of the seven-membered ring imide structure-containing group. A methylene group or methyl group with the mark "*2" is a hydrogen-donating atom adjacent to oxygen of an ether structure, nitrogen of an amine structure or sulfur of a thioether structure and bonded to N of the seven-membered ring imide structure-containing group at least via a non-aromatic skeleton.

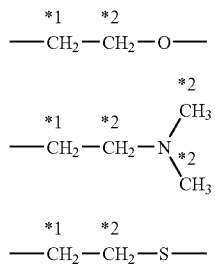

Formula (3)
Formula (4)
Formula (5)

Further, the chemical structure "X" may be a group containing one or more ethylenic unsaturated bond (ethylenic unsaturated group) such as a (meth)acrylate skeleton. A compound having a structure wherein an ethylenic unsaturated group is linked with a seven-membered ring imide structure-containing group is preferably used as a monomer component of a photosensitive resin composition since the compound functions as a radical polymerizable compound as well as a photoradical generator. Also, the radical generator itself bonds to a matrix structure of a radical reactant via an ethylenic unsaturated group, thus, there is an effect that stability of a radical generator after curing becomes significantly high. Additionally, if number of ethylenic unsaturated bond contained in the structure increases, compatibility with multifunctional acryl monomer or the like improves and physical properties of a cured layer such as hardness or heat resistance becomes good. When number of ethylenic unsaturated bond contained in the structure is small, relatively a soft layer tends to be produced.

Examples of a monovalent chemical structure except for organic groups include siloxane, silane, borazine or the like.

The compound (a) may have two or more seven-membered ring imide structure-containing group represented by the formula (1).

The compound having two or more seven-membered ring imide structure-containing group is higher in sensitivity at light radiation than a compound having one seven-membered ring imide structure-containing group.

In the compound (a), as a compound having two or more seven-membered ring imide structure-containing group, there is a compound whose chemical structure "X" of the compound represented by the formula (2) further has one or more seven-membered ring imide structure-containing groups represented by the formula (1). If the compound (a) has two or more seven-membered ring imide structure-containing groups, the seven-membered ring imide structure-containing groups in one molecule of the compound (a) may be same or different from each other.

In the compound (a), mainly a seven-membered ring imide structure-containing group improves heat resistance, and mainly a chemical structure "X" improves solubility to a solvent and compatibility with other solid components in a resin composition. Hence, as the size of the chemical structure "X" becomes larger, the solubility to a solvent and compatibility with other solid component in a resin composition becomes higher, on the contrary, heat resistance tends to be lower.

Therefore, in view of improvement in heat resistance, solubility and compatibility of a resin composition containing the compound (a), it is preferable that a value resulting from dividing a molecular weight of the compound (a) by number of seven-membered ring imide structure-containing group in one molecule of the compound (a) is 2,000 or less, more preferably 1,000 or less.

Particularly, when the compound (a) is a compound represented by the formula (2) the chemical structure "X" of which is a structure further having one or more seven-membered ring imide structure-containing groups represented by the formula (1), it is preferable to adjust the size of "X" upon synthesis so that a value resulting from dividing a molecular weight of the compound (a) by number of seven-membered ring imide structure-containing group is 2,000 or less as mentioned above.

Straight-chain or branched alkyl groups are preferable from the viewpoint of, particularly, cost, availability, synthetic simplicity and solubility. Straight-chain or branched alkyl groups containing an ester bond, ether bond, amide bond, urethane bond and urea bond therein are more preferable. Also, from the viewpoint of heat resistance, straight-chain or branched alkyl groups such as those having a saturated or unsaturated cyclic structure are preferable and those having an ester bond, ether bond, amide bond, urethane bond and urea bond are more preferable.

In order to improve sensitivity of the compound (a) of the present invention which is a photoradical generator, it is effective to select substituents $R^1$ to $R^8$ and "X" bonded to N properly such that the seven-membered ring imide structure-containing group contained in the compound (a) takes a chemical structure which is excited by light to easily produce a radical.

In order to obtain practical sensitivity, it is preferable to make a selection of the above-mentioned substituents $R^1$ to $R^8$ and "X" so that a part of the absorption wavelength of the compound (a) overlaps on any of the emitting wavelengths of an exposure light source (irradiation light source) in a process. The absorption maximum of the compound (a) falls within a range of particularly preferably ±20% and still more preferably ±10% of the emitting wavelength closest to the absorption maximum.

The molar extinction coefficient of the compound (a) in any of the emitting wavelengths of an exposure light source (irradiation light source) in a process is preferably 0.1 or more from the viewpoint of sensitivity. Here, the molar extinction coefficient E is given by the relationship induced from the Lambert-Beer rule and expressed by the following formula:

$$A = \epsilon cb$$

where:
A=Absorbance;
b=Length of an optical path in an example (cm); and
c=Concentration of a solute (mol/L).

In usual, when a change in absorbance is recorded using a solution having the same concentration and a cell having the same length of an optical path with changing the wavelength of incident light, the absorbance varies according to the wavelength, showing a maximum molar extinction coefficient $\epsilon_{max}$ at a wavelength specific to a compound to be a subject of measurement. The aforementioned term "the molar extinction coefficient of the above-mentioned compound in the exposure wavelength is 0.1 or more" implies that the molar extinction coefficient when measured using a wavelength adopted when carrying out exposure by using the compound is 0.1 or more but does not imply that the maximum molar extinction coefficient $\epsilon_{max}$ is 0.1 or more.

In the case of a usual high pressure mercury lamp, there are three significant emissions at 365 nm (i rays), 405 nm (h rays) and 436 nm (g rays). However, in actual, emissions are also present at, for instance, 333 nm or the like. Therefore, a photo-crosslinking compound may have absorption maximum in the vicinity of these wavelengths. Also, when irradiating with an F2-excimer laser (157 nm), ArF excimer laser (193 nm), KrF excimer laser (248 nm) or the like, the photo-crosslinking compound may have an absorption in the vicinity of these wavelengths. To state specifically, the absorption maximum around 365 nm falls in a range of preferably 365±73 nm and more preferably 365±37 nm.

If the absorption wavelength is overlapped on the region covering at least one wavelength among 157 nm, 193 nm, 248 nm, 365 nm, 405 nm and 436 nm which are major emitting wavelengths of very popular exposure light sources for forming minute patterns as described above, this is convenient to utilize these wavelengths as exposure wavelengths. It is particularly preferable that the molar extinction coefficient at this wavelength is 0.1 or more.

THE INTERPRETATION OF THE ULTRAVIOLET SPECTRA OF NATURAL PRODUCTS (A. I. Scott, 1964) and the table described in THE ORGANIC COMPOUND IDENTIFICATION METHOD BY A SPECTRUM, fifth edition (R. M. Silverstein, 1993) may be used as the references showing a guide to determine as to what substituent is introduced to shift the absorption wavelength to a desired wavelength.

Since the compound (a) of the present invention functions a hydrogen-drawing type photoradical generator, a radical is scarcely generated only by heating. Also, even though the radical-generating part contains a seven-membered ring imide skeleton, the photoradical initiator is scarcely decomposed by heating similarly to a naphthalimide structure-containing group containing six-membered ring imide skeleton. Therefore, it has high heat resistance, imparts good preserving stability to a photosensitive resin composition when compounded in the resin composition, improves the stability of the cured film which will be finally obtained and also prevents the light-resistance of the coating layer from being impaired and coloring, fading, peeling and cracks of the coating layer.

The 5% reduction in weight temperature of the compound (a) of the present invention is preferably 50° C. or more and more preferably 130° C. or more in view of heat resistance.

Herein, the 5% reduction in weight temperature means a temperature at which the weight of a sample is reduced to 5% of the initial weight when a decrement of weight is measured using a thermogravimetric analyzer according to the same method as in the examples of the present invention as will be explained later. Similarly, the 10% reduction in weight temperature means a temperature at which the weight of a sample is reduced to 10% of the initial weight.

The compound (a) preferably has high solubility when compounded in the resin composition with the intention of improving coating suitability, transparency of the cured film, sensitivity during exposure or the like.

The solubility of the compound (a) in a solvent is preferably high from the viewpoint of coating suitability during application. Specifically, the solubility of the compound (a) in a solvent to be used, particularly in any of common solvents as will be described later is preferably 0.1% by weight or more.

Also, even in the case of a resin composition dissolved in a transparent state by using a solvent, precipitates are produced in the coating layer during drying when the solvent is evaporated at a coating process in the case where the compatibility among solids contained in the resin composition is low and only insufficient transparency is obtained. For this, when a coating layer or a molded body having such high transparency as that of an optical member is needed, it is preferable to use the compound (a) having high compatibility with other solid components in the resin composition, particularly, a polymerizable compound such as a compound having an ethylenic unsaturated bond or the like. When high transparency is needed, all ray-transmittance (JIS K7105) is preferably 90% or more and more preferably 95% or more when the layer thickness of the coating layer formed by curing the photosensitive resin composition is 10 µm.

In the case where the solubility of the compound (a) in a polymerizable compound is high, the function as the initiator is improved and therefore has high sensitivity at the time of exposing. From this point, a saturated concentration of the compound (a) in methyl acrylate at 20° C. is 0.01 mol/L or more when evaluating solubility by using methyl acrylate as a typical monomer component.

The solubility or compatibility of the compound (a) can be improved by introducing a substituent into a seven-membered ringimide structure-containing group. From this point of view, a saturated or unsaturated alkyl group having 1 to 15 carbon atoms, alkoxy group, bromo group, chloro group, fluoro group, nitro group, primary to tertiary amino group or the like is preferable as a substituent of the seven-membered ring imide ring structure-containing group. The solubility or compatibility of the compound (a) also can be improved by changing the structure of "X" in formula (2) or by introducing a substituent into the "X". The substituent introduced into or the structural reformation made to the seven-membered ring imide ring structure-containing group or "X" structure of the compound (a) are selected variously corresponding to a solvent in which the compound (a) is intended to be dissolved and other solid components which is intended to be solved mutually. For example, when selecting a carboxyl group as the substituent, it is easily solved in water and organic polar solvents whereas when introducing an ester, its solubility in a solvent or compound having an ester bond is improved.

A compound (a) having a seven-membered ring imide ring structure-containing group of the present invention can be synthesized using various known methods. For example, the synthesis may be of imidization by reacting diphenic anhydride or the derivatives thereof with various amine or imidization of diphenic anhydride followed by introducing a substituent according to an objective function. Also, a dehydration and ring-closure reaction upon the imidization reaction may be performed by heat or using a dehydrating catalyst such as acetic acid anhydride or the like.

Measures for synthesizing the compound (a) will be hereinafter exemplified; however, these measures are not intended to be limiting of the synthetic method according to the present invention.

First, diphenic anhydride is poured into N,N-dimethylformamide and stirred. Thereto, 2-methoxyethylamine in an amount by mol equivalent to the diphenic anhydride is added dropwise, and stirred at 0 to 70 ☐ for about 1 to 15 hours. The reaction solvent used at this time is not limited to dimethylformamide. As the reaction solvent, solvents such as organic polar solvents in which a final product is dissolved are preferable. Because the diphenic anhydride has relatively poor solubility and is sparingly soluble in a general solvent, there are many cases where it is made soluble by reacting with an amine.

As aforementioned, acid anhydride used herein may be not only diphenic anhydride but also may be one having substituents $R^1$ to $R^8$ introduced preliminarily according to the object. Also, a substituent may be introduced to $R^1$ to $R^8$ of the seven-membered ring imide ring structure-containing group represented by the formula (1) to shift an absorption wavelength of light and change an extinction coefficient before or after the imidization reaction.

Meanwhile, no particular limitation is imposed on the amine compound or 2-methoxyethylamine and various amine, diamine, triamine, polyamine compounds or the like may be used corresponding to the purpose. For example, the following amines may be used but may not be limited.

Examples of amines having a hydroxyl group include oxyalkylamines such as 2-aminoethanol, propanolamine, hexanolamine or the like, and substituted oxyalkylamines such as ethoxyethanolamine, propoxypropanolamine, 2-(2-aminoethoxy)ethanol or the like.

Examples of amines having a carboxyl group include amino acid compounds such as α-alanine, β-alanine, serine, glycine or the like.

Examples of amines having secondary or tertiary amino group include N,N-dimethylaminoethylene diamine, diethylene triamine or the like.

Examples of amines having an ether bond include 2-amino-1-methoxypropane, aminomethyl vinyl ether, aminoethyl vinyl ether, aminobutyl vinyl ether, aminohexyl vinyl ether, aminocyclohexyl vinyl ether, aminononyl vinyl ether and those obtained by substituting the vinyl groups of these compounds with an alkyl or aryl group at the α-position or β-position of each compound. Specifically, there may be an aminoalkyl propenyl ether, aminoalkyl isopropenyl ether, aminoalkyl styryl ether or the like, but may not be particularly limited.

Other examples include 2-aminoethanethiol having a mercapto group, 2-aminoethylhydrogen sulfate having a sulfonic group and 2-aminoethyldihydrogen phosphate having a phosphoric acid group.

After stirring as above at predetermined temperature for several hours, acetic acid anhydride is added excessively as a dehydrator, which was then stirred at 80 to 150° C. for 1 to 15 hours. The solvent and acetic acid anhydride in the reaction solution were distilled by a rotary evaporator, DMF was added therein and the reaction solution was poured into water to re-precipitate followed by filtration to obtain a solid. The solid is subject to re-crystallization from a desired solvent, thus, seven-membered ring imide ring can be obtained almost quantitatively. The refining method is not limited to recrystallization but all known methods such as sublimation refining, column chromatography or the like may be used. However, recrystallization is preferable in view of cost.

If it is not imidization by heating as exemplified herein but chemical imidization using a dehydrating catalyst, the dehydrating catalyst is not limited to acetic acid anhydride. There may be propionic anhydride, n-butyric anhydride, benzoic anhydride or the like, but may not be limited.

The photoradical polymerization initiator obtained in this manner according to the present invention can cause a radical reaction by applying light such as electromagnetic waves, radial rays or the like to excite it because the seven-membered ring imide structure-containing group of the compound (a) functions as a hydrogen-drawing type radical-generating part, thus, can be suitably used as a photoradical initiator.

The seven-membered ring imide structure-containing group generates a radical by light radiation but does not generate a radial when heated in a practical range since it is a hydrogen-drawing type. Also, it is generally considered that a seven-membered ring imide structure is lower in stability compared with a six-membered ring structure, however, a seven-membered ring imide structure containing group of a photoradical generator of the present invention is highly stable and hardly causes heat decomposition. Hence, the photoradical generator of the present invention is high in heat resistance, stability and preserving ability from the viewpoint of a radical generating mechanism as well as a chemical structure of a radical generating part.

It is inferred that the reason for the seven-membered ring imide structure-containing group to have high stability is that the seven-membered ring imide structure-containing group, which is derived from diphenic anhydride having a carboxyl group at the 2,2' position of biphenyl, can have stable structure by twisting two aromatic rings contained in the biphenyl structure (FIGS. 1 and 2). Here, FIG. 1 is a model showing the conformation of an example of a compound (a) viewed from above the aromatic rings. FIG. 2 is a model showing the conformation of the same compound viewed from the direction of an ax which bonds the aromatic rings.

A photoradical generator of the present invention is particularly excellent in compatibility and solubility in comparison with a compound having a naphthalimide structure-containing group, which has a six-membered ring(s), and has wide range in mixing ratio with other components such as polyfunctional monomer, acrylic resins or the like. For example, it is possible to contain the photoradical generator of the present invention in a photosensitive resin composition by 30% by weight or more.

Therefore, the photoradical generator of the present invention can improve the sensitivity by containing large quantities of radical generating parts in a resin composition. It is inferred that the reason for the photoradical generator of the present invention to have excellent compatibility and solubility is that n surface of an aromatic ring contained in a seven-membered ring imide structure-containing group is twisted and is thus less likely to form n-n stacking than naphthalimide of six-membered ring having wide n surface without a twist.

Further, the photoradical generator of the present invention is superior in transparency to a compound having a naphthalimide structure-containing group of six-membered ring. It is inferred that the reason for the photoradical generator of the present invention to have excellent transparency is that an aromatic ring (s) contained in a seven-membered ring imide structure-containing group is twisted and n conjugated system is cut, thus, absorption of ultraviolet ray shifts to relatively a short wave side. When transparency is high, sensitivity to radiation wavelength of ultraviolet ray generally tends to not good, however, the photoradical generator of the present invention has good sensitivity beside high transparency. Hence, it is advantageous to use the photoradical generator of the present invention for the use which requires transparency to visible light to a photosensitive resin composition and a final product. It is also possible to increase transparency of the photoradical generator by molecule design so that a compound (a) does not have absorption in a visible light area.

Since the radical generated by the a seven-membered ring imide structure-containing group acts in accordance with a hydrogen-drawing mechanism, it can react not only with a general polymerizable group such as an ethylenic unsaturated bond or the like but also with various compounds such as aromatic rings. Hence, the compound (a) can be not only used as a usual photoradical polymerization initiator but also as an initiator or promoter of various radical reactions. For example, it can be used as a crosslinking agent for a resin composition containing low-molecular weight aromatic compounds such as methylbenzene or aromatic polymers having an aromatic part such as PET to thereby improve solvent resistance after curing.

Also, the photoradical polymerization initiator comprising the compound (a) is a hydrogen-drawing type and is bonded to a reaction product such as a polymer generated by a radical reaction or the like to constitute a part of the chemical structure of the reaction product. For this, when the compound (a) is used as the photoradical polymerization generator, the low-molecular weight decomposition material does not remain in a free state after the radical reaction and it is not necessary to evaporate at the time of the post-baking unlike the case of using a self-cleavage type initiator (type I). Also, even if the compound (a) remains unreacted, a radical is not generated in the processes thereafter since the radical-generating part has a seven-membered ring imide structure having high heat resistance.

Namely, as for the residues originated from the photoradical polymerization generator comprising the compound (a) according to the present invention, the part consumed by a radical reaction and an unreacted part are both present in a chemically stable state in the cured coating layer of the photosensitive resin composition and no volatile decomposition material is produced.

Therefore, various problems due to decomposition materials or unreactants after reaction derived from a photoradical initiator such as a problem concerning operational safety, problems concerning a decline in the reliability of a final product such as deterioration of heat resistance or light resistance, occurrence of coloring or fading and peeling or cracks of a coating layer or the like, a problem as to shorten life of a chemical solution and a problem concerning the generation of an odor (out gas) can be all solved.

As aforementioned, a photoradical generator comprising a compound (a) having a seven-membered ring imide structure-containing group of the present invention generates a radical by a hydrogen-drawing type radical mechanism to initiate or proceed various radical reactions such as radical polymerization reaction, radical crosslinking reaction or the like and problematic compounds such as an unstable unreactant, a volatile low-molecular weight decomposition material or the like are not left after reaction.

In addition, the compound (a) is significantly excellent in compatibility and solubility, which have been considered to be not sufficient, besides having heat resistance, stability and preserving ability almost equal to a compound having a six-membered ring structure imide group, which has good heat resistance conventionally, and further has high transparency, thus, the compound highly serves many uses.

Next, a photosensitive resin composition according to the present invention (hereinafter, simply referred as "resin composition") will be explained.

The resin composition according to the present invention contains the compound (a) having a seven-membered ring imide structure-containing group represented by the formula (1) and the compound (b) having an ethylenic unsaturated bond as essential components. The resin composition may further contain, according to the need, a hydrogen donor, a curable reactive compound except for the compound (b), a radical generator except for the compound (a), a macro molecular weight binder component or other components.

In the resin composition of the present invention, the seven-membered ring imide structure-containing group of the photoradical initiator comprising the compound (a) functions as a hydrogen-drawing type radical-generating part and radicalized when excited by applying light such as electromagnetic waves and radial rays to cause a radical reaction in the resin composition. The compound (b) having an ethylenic unsaturated bond in the resin composition causes radical polymerization thereby curing the resin composition and changing solubility.

When the resin composition further contains a radical reactive compound other than the compound (b) having an ethylenic unsaturated bond as a curable reactive compound or a macro molecular weight binder component, the radical reactive compound causes various radical reactions such as a radical dimerization reaction with the compound (a) which is a radical generator and a radical crosslinking reaction according to the type of compound and therefore cures the resin composition and changes solubility in combination with the compound (b).

Here, the crosslinking means that a crosslinking bond is generated, wherein the crosslinking bond means a bond formed in such a manner as to build a bridge between optional two atoms among a molecule consisting of atoms bound chain-wise. The bond in this case may be formed in the same molecule or between different molecules (CHEMICAL HANDBOOK, Tokyo Kagaku Dojin Co., Ltd., p. 1082).

The compound (b) having an ethylenic unsaturated bond has been widely utilized as a curable reactive compound which is radically polymerizable and has a wide range of application. Therefore, the compound (b) is used as an essential curable reactive compound in the photosensitive resin composition of the present invention. As the compound (b) having an ethylenic unsaturated bond, compounds having one or more ethylenic unsaturated bonds and compounds having at least one ethylenic unsaturated bond and other functional groups may be used. There may be exemplified amide type monomers, (meth)acrylate monomers, urethane (meth)acrylate oligomers, polyester (meth)acrylate oligomers, epoxy (meth)acrylates and hydroxyl group-containing (meth)acrylates and aromatic vinyl compounds such as styrene. Herein, (meth)acrylate may be acrylate or methacrylate.

Examples of the amide type monomer include amide compounds such as N-vinyl pyrrolidone, N-vinyl caprolactam, acryloylmorpholine or the like.

Examples of the (meth)acrylate monomer include imide acrylates such as hexahydrophthalimideethyl acrylate, succinic imideethyl acrylate or the like; hydroxyalkyl(meth) acrylates such as 2-hydroxyethyl(meth)acrylate, 2-hydroxypropyl(meth)acrylate, 2-hydroxy-3-phenylpropylacrylate or the like; acrylates of phenyl alkylene oxide adducts such as phenoxyethyl(meth)acrylate or the like and their halogen nucleus substitution derivatives; mono or di(meth)acrylates of glycols such as mono or di(meth)acrylates of ethylene glycol, mono(meth)acrylates of meth oxyethylene glycol, mono or di(meth)acrylates of tetra ethylene glycol and mono or di(meth)acrylates of dipropyrene glycol; (meth)acrylates of polyol or their alkylene oxides such as trimethylolpropanetri(meth)acrylate, pentaerythritol tri(meth)acrylate, pentaerythritol tetra(meth)acrylate, dipentaerythritol hexaacrylate or the like, and isocyanuric acid EO-denatured di or tri(meth)acrylates.

Examples of the urethane (meth)acrylate oligomer include reaction products obtained by further reacting a hydroxyl group-containing (meth)acrylate with a reaction product between a polyol and an organic polyisocyanate.

Here, the polyol includes low-molecular weight polyols, polyethylene glycols, polyester polyols or the like. Examples of the low-molecular weight polyol include ethylene glycol, propylene glycol, cyclohexanedimethanol, 3-methyl-1,5-pentanediol or the like. Examples of the polyether polyol include polyethylene glycols, polypropylene glycols or the like. Examples of the polyester polyol include reaction products between these low-molecular weight polyols and/or polyether polyol and acid components, for example, dibasic acids such as adipic acid, succinic acid, phthalic acid, hexahydrophthalic acid, terephthalic acid or the like or their anhydrides.

Also, examples of the organic polyisocyanate to be reacted with the aforementioned polyol include tolylene diisocyanate, 4,4'-diphenylmethanediisocyanate, 4,4'-dicyclohexylmethanediisocyanate, hexamethylene diisocyanate, isophorone diisocyanate or the like.

Examples of the polyester (meth)acrylate oligomer include dehydration condensates between polyester polyols and (meth)acrylic acids. Examples of the polyester polyol include low-molecular weight polyols such as ethylene glycol, polyethylene glycol, cyclohexanedimethanol, 3-methyl-1,5-pentanediol, propylene glycol, polypropylene glycol, 1,6-hexanediol, trimethylolpropane or the like and reaction products between polyols such as alkylene oxide adducts of these low-molecular weight polyols and acid components such as dibasic acids, e.g., adipic acid, succinic acid, phthalic acid, hexahydrophthalic acid, terephthalic acid or the like or their anhydrides.

The epoxy(meth)acrylate is those obtained by addition-reacting unsaturated carboxylic acids such as (meth)acrylic acids with epoxy resins. There may be exemplified epoxy (meth)acrylates of bisphenyl A type epoxy resins, epoxy (meth)acrylates of phenyl or cresol novolac type epoxy resins, (meth)acrylic acid addition reaction materials of diglycidyl ether as a polyether or the like.

The compound (b) preferably has two or more and particularly three or more ethylenic unsaturated bonds from the viewpoint of crosslinking radical polymerizable compounds or radical reactive (except for radical polymerization) compounds three-dimensionally.

As the compound (b), those having alkali-soluble and hydrophilic functional groups such as a carboxyl group, phenylic hydroxyl group, sulfonic acid group and hydroxyl group may be used to improve the alkali developing ability of the photosensitive resin composition in the case of using the resin composition as a resist forming a pattern by exposure in applications such as electronic parts, color filters or the like.

It is preferable that the compound (b) does not have absorption in a wavelength range where the radiating wavelength is overlapped on the absorption wavelength of the seven-membered ring imide structure containing group in order not to inhibit sensitivity of the resin composition to radiating light.

The photosensitive resin composition may be compounded with a macro molecular compound or a curable reactive compound having a reaction form except from a radical reaction as a binder resin to control the film forming property of the composition put in an uncured state and the physical properties of the coating layer after cured. A radical generated by a seven-membered ring imide structure-containing group can be reacted not only with an ethylenic unsaturated bond but also with various compounds such as aromatic rings and enables a macro molecular compound to be crosslinked by a radical reaction even in the case of a macro molecular compound compounded as a binder resin having no ethylenic unsaturated bond.

A known macro molecular compound or a curable reactive compound having a reaction form except from a radical reaction may be used as the binder component. As the macro molecular compound, all known macro molecular compounds may be used. There may be exemplified, though not limited to, all known macro molecular compounds or a curable reactive compounds having a reaction form except from a radical reaction such as organic polyisocyanates such as tolylenediisocyanate, 4,4'-diphenylmethanediisocyanate, 4,4'-dicyclohexylmethanediisocyanate, hexamethylene diisocyanate, isophorone diisocyanate or the like; polymers and copolymers of acryl or vinyl compounds such as vinyl acetate, vinyl chloride, acrylates, methacrylates or the like; styrene type resins such as polystyrene or the like; acetal resins such as formal resins, butyral resins or the like; silicone resins; phenoxy resins; epoxy resins typified by bisphenyl A type epoxy resins or the like; urethane resins such as polyurethane or the like; phenyl resins; ketone resins; xylene resins; polyamide resins and the precursors; polyimide resins and the precursors; polyether resins; polyphenylene ether resins; polybenzoxazole resins; cyclic polyolefin resins; polycarbonate resins; polyester resins; polyarylate resins; polystyrene resins; novolac resins; alicyclic polymers such as polycarbodiimide, polybenzoimidazole, polynorbornane or the like; siloxane type polymers or the like. These compounds may be used either independently or in combinations of two or more. Each of these macro molecular compounds preferably has a weight average molecular weight of 3,000 or more generally though depending of the uses of the resin composition. An excessively large molecular weight brings about a deterioration in solubility and processability, thus, a weight average molecular weight of 10,000,000 or less is generally preferable.

The amount of the compound (a) in the resin composition is preferably 0.1% by weight or more based on the whole solid of the resin composition from the viewpoint of obtaining sufficient radical generating amount in order to obtain a good curing speed and high crosslinking density and improve a coating layer strength and glass transition temperature. The amount of the compound (a) is more preferably 1% by weight or more from the viewpoint of sensitivity and the physical properties of the coating layer. In this case, the mixing ratio of the compound (a) to the compound (b) is optionally selected according to the object taking various material physical properties into account. It is to be noted that the solid content of the photosensitive resin composition means the whole components other than solvents and a liquid monomer component is included in the solid content.

In the case of using a combination of the compound (b) and other radical reactive compounds as the curable reactive compound, the amount of the compound (a) is appropriately adjusted according to the type and amount of the radical reactive compound to be combined.

The amount of the compound (b) is preferably 1% by weight or more based on the whole solid content of the resin composition to obtain sufficient photocurability. The photosensitive resin composition may contain a macro molecular weight binder component other than the component (b). In this case, the amount of the binder component is preferably 1% by weight or more and 97% by weight or less based on the solid content of the whole of the resin composition according to the use. When the amount of the macro molecular weight binder component containing no ethylenic unsaturated bond is more than 97% by weight, photocurability tends to be deteriorated.

Also, since the compound (a) is a hydrogen-drawing type radical generator, it is preferable to compound a hydrogen donor in the resin composition of the present invention from the viewpoint of more improving the efficiency of generation of radicals and bettering sensitivity. Depending on the type of the compound (a), there may be a case that radical generating efficiency improves more than a hydrogen donor. In this case, it is particularly effective to use a hydrogen donor.

Examples of the hydrogen-donating group of the hydrogen donor include functional groups such as an alkyl group in which hydrogen is directly bonded to carbon and organic groups having an amine, thiol, hydroxyl group or ether bond which is usually used as a hydrogen-donating group. Particularly, organic groups having a thiol, amine, hydroxyl group and an ether bond which easily provide hydrogen are preferable in view of sensitivity. It is said that as to the ether bond, hydrogen of a hydrocarbon structure (alkane and alkene) adjacent to the ether bond is easily drawn. Therefore, the hydrogen-donating group containing an ether bond preferably has a structure having such a hydrogen.

As the amine used as the hydrogen donor, a primary, secondary and tertiary amine can be used. Examples of the tertiary amine are triethylamine, N,N-dimethylcyclohexylamine, dimethylbenzylamine, N,N-dimethyl toluidine, pentamethyldiethylamine, pentamethyldiethylenetriamine, morpholine, pyridine or the like.

As examples of the tertiary amine having functional groups such as a hydroxyl group, there may be triethanolamine, N,N-dimethylaminoethanol or the like. Further, tertiary amine which is a reactive monomer having an amino group such as 2,2-dimethylaminoethyl(meth)acrylate, 2,2-diethylaminoethyl(meth)acrylate or the like.

The proportion of the hydrogen-donating group contained in the hydrogen donor is preferably the same as or more than the number of the moles of the seven-membered ring imide part in the resin composition from the viewpoint of sensitivity. However, a proper value can be arbitrarily selected depending on relation between sensitivity and the physical properties of the coating layer obtained finally.

When the resin composition of the present invention is cured by light radiation, other photoradical generator may be used as required together with the compound (a) to promote a radical reaction. When other photoradical generator is used together with the compound (a), the other photoradical generator possibly produces decomposition materials, giving rise to problems concerning discoloration and physical properties of the cured film, vaporization of decomposition materials and stability and preserving ability of the photosensitive resin composition or the like. However, because the amount of the other photoradical generator can be decreased by using the compound (a) together, the above problems arise with more difficulty than in the case of using only other photoradical generator. Even if these problems arise, the problematic level is low. Therefore, the problems due to the photoradical generator can be suppressed to a practically allowable level while a sufficient radical reactivity is allowed to be exhibited.

Examples of the other photoradical generator include benzoins and their alkyl ethers such as benzoin, benzoin methyl ether, benzoin ethyl ether, benzoin isopropyl ether or the like; acetophenones such as acetophenone, 2,2-dimethoxy-2-phenylacetophenone, 2,2-diethoxy-2-phenylacetophenone, 1,1-dichloroacetophenone, 1-hydroxyacetophenone, 1-hydroxycyclohexyl phenyl ketone, 2-methyl-1-[4-(methylthio)phenyl]-2-morpholino-propan-1-on e or the like; anthraquinone such as 2-methylanthraquinone, 2-ethylanthraquinone, 2-tertiary butylanthraquinone, 1-chloroanthraquinone, 2-amylanthraquinone or the like; thioxanthone such as 2,4-dimethylthioxanthone, 2,4-diethylthioxanthone, 2-chlorothioxanthone, 2,4-diisopropylthioxanthone or the like; ketals such as acetophenonedimethylketal, benzylmethylketal or the like; monoacylphosphine oxides such as 2,4,6-trimethylbenzoyldiphenylphosphine oxide or bisacylphosphine oxides; benzophenones such as benzophenone or the like; and xanthones.

These photoradical generators may be used in combination with a photopolymerization-initiation promoter such as benzoic acid types and amine types. The proportion of these photoradical initiators is preferably 0.1% by weight or more and 35% by weight or less and more preferably 1% by weight or more and 10% by weight or less based on the whole solid content of the resin composition.

Other than the above, various organic or inorganic low-molecular or macro molecular compounds may be compounded to provide processability and various abilities to the resin composition according to the present invention. For example, dyes, surfactants, leveling agents, plasticizers, microparticles and sensitizers or the like may be used. Examples of the microparticles include organic microparticles such as polystyrene, polytetrafluoroethylene or the like and inorganic microparticles such as colloidal silica, carbon, phyllosilicate or the like. Examples of the function or form of these microparticles include pigments, fillers and fibers.

The proportion of these optional components is preferably in a range from 0.1% by weight to 95% by weight based on the whole solid content of the resin composition. If the proportion is less than 0.1% by weight, it is difficult to exhibit the effect of the added additives whereas if the proportion exceeds 95% by weight, it is difficult to reflect the characteristics of the resin composition upon a final product.

When components absorbing a radiated light are compounded in a large amount in the resin composition, the light insufficiently reaches the compound (a) which is a photoradical generator, decreasing sensitivity. Components other than the compound (a) preferably has a transmittance of 20% or more in a wavelength range where the emitting wavelength of a irradiation light source is overlapped on the absorption wavelength of the photoradical generator of the present invention contained in the resin composition from the viewpoint of regarding the sensitivity of the resin composition as important.

The resin composition according to the present invention may be diluted with a solvent to bring the concentration to a proper one. Examples of the solvent are various common solvents including ethers such as diethyl ether, tetrahydrofuran, dioxane, ethylene glycol dimethyl ether, ethylene glycol diethyl ether, propylene glycol dimethyl ether and propylene glycol diethyl ether; glycol monoethers (so-called cellosolves) such as ethylene glycol monomethyl ether, ethylene glycol monoethyl ether, propylene glycol monomethyl ether, propylene glycol monoethyl ether, diethylene glycol monomethyl ether, ethylene glycol monoethyl ether or the like; ketones such as methyl ethyl ketone, acetone, methyl isobutyl ketone, cyclopentanone, cyclohexanone or the like; esters such as ethyl acetate, butyl acetate, n-propyl acetate, i-propyl acetate, n-butyl acetate, i-butyl acetate, acetates of the aforementioned glycol monoethers (e.g., methylcellosolve acetate and ethylcellosolve acetate), methoxypropyl acetate, ethoxypropyl acetate, dimethyl oxalate, methyl lactate, ethyl lactate or the like; alcohols such as ethanol, propanol, butanol, hexanol, cyclohexanol, ethylene glycol, diethylene glycol, glycerol or the like; halogenated hydrocarbons such as methylene chloride, 1,1-dichloroethane, 1,2-dichloroethylene, 1-chloropropane, 1-chlorobutane, 1-chloropentane, chlorobenzene, bromobenzene, o-dichlorobenzene, m-dichlorobenzene or the like; amides such as N,N-dimethylformamide, N,N-dimethylacetamide or the like; pyrrolidones such as N-methylpyrrolidone or the like; lactones such as γ-butyrolactone or the like; sulfoxides such as dimethylsulfoxide or the like; and other organic polar solvents; and further aromatic hydrocarbons such as benzene, toluene, xylene or the like and organic non-polar solvents. Also, compounds having a reactive group in their structures, such as ethylenic unsaturated compounds or the like which are liquids at ambient temperature may be used as a reactive diluent. These solvents are used either independently or in combinations. Also, these solvents may be used after they are filtered to remove impurities by known various methods, for example, using a filter having a pore diameter of about 0.05 µm to 0.2 µm in general.

The resin composition may be prepared by mixing a photoradical generator comprising the compound (a) as an essential component and the compound (b) having an ethylenic unsaturated group with a curable reactive compound and optional components such as macro molecular binder component corresponding to the uses or the like.

A resin composition of the present invention contains a photoradical generator comprising a compound (a) which is high in heat resistance and quite high in solubility and compatibility with solvents and other compounded components, hence, heat resistance, stability and preserving ability are high in the state of a resin composition.

When the resin composition is coated in a predetermined pattern or formed in a predetermined form and radiated with light, a photoradical generator comprising a compound (a) to start reaction and cause various radical reactions such as a radical dimerization reaction, a radical crosslinking reaction or the like according to the compounded components so as to thereby cure the resin composition and/or change solubility. A seven-membered ring imide structure-containing group of a compound (a) generates a radical without generating by-product of low-molecular decomposition material upon the photoradical reaction, thereafter, the seven-membered ring imide structure-containing group is bonded to a curable component of a compound (b) or the like and becomes a part of chemical structure of a matrix of a cured product. Also, even if the seven-membered ring imide structure-containing group of a compound (a) is unreacted, no radical is generated in a heating process thereafter if the heating temperature is in a general range.

Therefore, there is no problem that a volatile low-molecular decomposition material or unstable unreactant derived from a radial initiator to remain in a cured product of the resin composition. As the result, there is an effect to raise heat resistance of cured product or layer or stability, thus, the problem concerning a decline in the reliability of a final product is solved. Also, since the generation of an odor (outgas) is not caused, a problem concerning operational safety improves.

Further, since a compound (a) has high sensitivity of temperature in a practical range besides high transparency, an effect of improved transparency of final product can be expected.

The resin composition according to the present invention may be used in all known fields and products, such as pattern-forming materials (resists), coating materials, printing inks, adhesives, fillers, molding materials and three-dimensional articles, materials which are cured or changed in solubility by radiation with active energy beam. Particularly, it is suitable for those which are required heat resistance and a high reliability, such as forming paints, printing inks, color filters, electronic parts, layer insulation films, wire cover films, optical members, optical circuits, optical circuit parts, antireflection films, holograms or building materials.

In the case of, for example, the color filter, a pixel portion, light-shading portion (black matrix) disposed at a boundary of pixels, a protective layer and a spacer for keeping a cell gap may be formed of a cured product of the above described photosensitive resin composition.

In the case of the electronic parts, an under-filling agent, a sealing agent or the like used in semiconductor devices may be exemplified.

As to the layer insulation films, layer insulation films for build-up substrates, layer insulation films in fuel cells and insulation coatings of car parts or domestic electric products, for which the heat resistance and the reliability to insulation are required, may be formed of a cured product of the photosensitive resin composition.

Also, as the wire protective films, solder resists which are wire protective layers on the surface of printed boards, wire surface covers or the like may be exemplified.

In the case of the optical members, overcoats of various optical lenses, antireflection films, optical waveguides, optical circuit parts such as wave dividers or the like, relief type or volume type holograms or the like may be exemplified.

In the case of the building materials, wall papers, wall materials, floor materials and other surface covering materials reduced in volatile components, adhesives/pressure sensitive adhesives and inks may be exemplified.

The print product, color filter, electronic parts, layer insulation film, wire cover film, optical member, optical circuit, optical circuit parts, antireflection film, hologram or building material according to the present invention has high heat resistance and stability and therefore has such a merit that productive yield is high since at least a part of each is formed of a cured product of the photosensitive resin composition having high heat resistance and stability.

EXAMPLE

Example 1

A 1 L eggplant-shape flask was charged with 11.2 g (0.05 mol) of diphenic anhydride, 300 ml of N,N-dimethylformamide (hereinafter referred to as DMF) and a catalytic amount of pyridine, and stirred. Thereto, 3.8 g (0.05 mol) of 2-methoxyethylamine was added dropwise, which was then stirred at ambient temperature for 4 hours and then 100 ml of acetic anhydride was added to be stirred at 120° C. for 5 hours. DMF, acetic anhydride and the like were removed by a rotary evaporator. The sample was dissolved to DMF in an appropriate concentration, dropped in distilled water, and re-precipitated to be refined. After that, re-crystallization was followed, thus, 13.7 g of a compound 1 represented by the following formula (one of the compound (a)) as needle crystals was obtained:

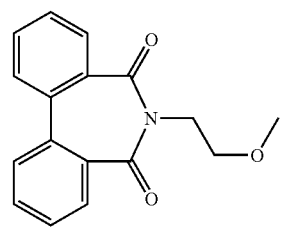

Compound 1

Example 2

A reaction was run in the same condition as in the Example 1 except that the amine as the starting material was altered to 2-ethanolamine. Each raw material was supplied in the same number of moles as in Example 1. In the reaction, a compound 2 (one of the compound (a)) wherein a hydroxyl group in the end was acetylated by acetic anhydride was quantitatively obtained since an amine having hydroxyl groups in the ends was used:

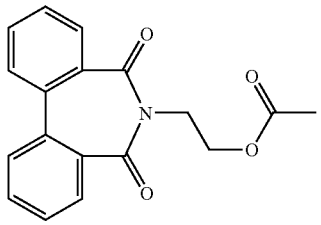

Compound 2

Example 3

A reaction was run in the same condition as in the Example 1 except that the amine as the starting material was altered to 2-(2-aminoethoxy)ethanol. Each raw material was supplied in the same number of moles as in Example 1. In the reaction, a compound 3 (one of the compound (a)) wherein a hydroxyl group in the end was acetylated by acetic anhydride was quantitatively obtained since an amine having hydroxyl groups in the ends was used:

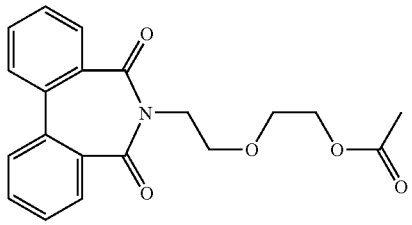

Compound 3

Example 4

A reaction was run in the same condition as in the Example 1 except that the amine as the starting material was altered to valinol. Each raw material was supplied in the same number of moles as in Example 1. In the reaction, a compound 4 (one of the compound (a)) wherein a hydroxyl group in the end was acetylated by acetic anhydride was quantitatively obtained since an amine having hydroxyl groups in the ends was used:

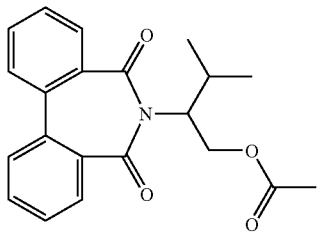

Compound 4

Example 5

A reaction was run in the same condition as in the Example 1 except that the amine as the starting material was altered to 3-amino-1-propanol vinyl ether. Each raw material was supplied in the same number of moles as in Example 1. As the result, a compound 5 (one of the compound (a)) represented by the following formula was obtained:

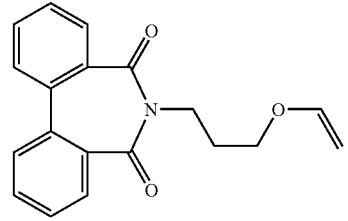

Compound 5

Example 6

A reaction was run in the same condition as in the Example 1 except that the amine as the starting material was altered to 2-[2-(2-aminoethoxy)ethoxy]ethanol. Each raw material was supplied in the same number of moles as in Example 1. As the result, a compound 6 (one of the compound (a)) represented by the following formula was obtained.

2-[2-(2-aminoethoxy)ethoxy]ethanol used in the Example was synthesized in the following manner:

A 500 ml eggplant-shape flask was charged with 16.9 g (0.1 mol) of 2-[2-(2-chloroethoxy)ethoxy]ethanol, 22.3 g (0.12 mol) of potassium phthalimide and 100 ml of DMF, and stirred for 24 hours at 120° C. After reaction, a white precipitate was filtered, condensed by a rotary evaporator so as to have about 50 ml of filtrate and 500 ml of dichloromethane was poured. The sample generated white precipitate was filtered and the filtrate was condensed, thus, a phthalimide compound having a side chain of ethylene glycol which is a precursor material of aimed product was obtained. The precursor material was dissolved in 500 ml of ethanol, and 5.5 g (0.11 mol) of hydrazine monohydrate was added to be refluxed while stirring for 7 hours followed by cooling to ambient temperature and filtering a white precipitate, thus, 2-[2-(2-aminoethoxy)ethoxy]ethanol was almost quantitatively obtained.

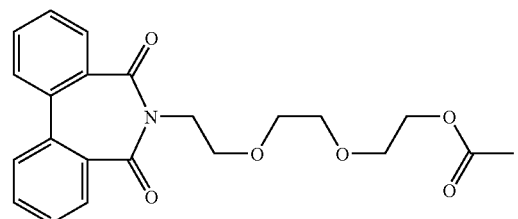

Compound 6

Example 7

A 1 L eggplant-shape flask was charged with 11.2 g (0.05 mol) of diphenic anhydride, 300 ml of DMF and a catalytic amount of pyridine, and stirred. Thereto, 3.1 g (0.05 mol) of 2-ethanolamine was added dropwise, which was then stirred at ambient temperature for 4 hours and then 100 ml of acrylic anhydride was added to be stirred at 40° C. for 24 hours. After reaction, the reaction solution was added dropwise to a saturated sodium hydrogencarbonate solution to re-precipitate, thereafter, purified by column chromatography using chloroform, and thus obtained a compound 7 represented by the following formula (one of a compound (a)).

The acrylic anhydride used herein was obtained by reacting sodium acrylate and acrylic acid chloride in dried diethyl ether.

Compound 7

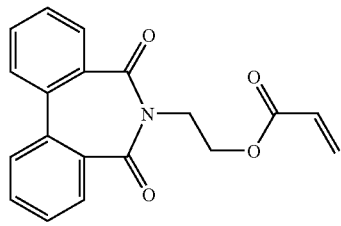

Example 8

A reaction was run in the same condition as in the Example 7 except that the amine as the starting material was altered to 2-ethanolamine. Each raw material was supplied in the same number of moles as in Example 7. As the result of the reaction, a compound 8 (one of the compound (a)) was obtained:

Compound 8

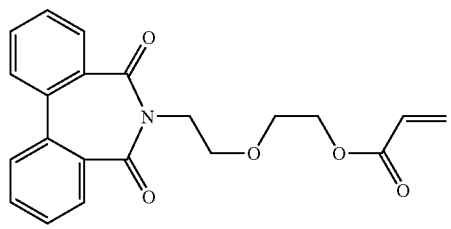

Example 9

A reaction was run in the same condition as in the Example 7 except that the amine as the starting material was altered to 2-[-(2-aminoethoxy)ethoxy]ethanol. Each raw material was supplied in the same number of moles as in Example 7. As the result, a compound 9 (one of the compound (a)) was obtained:

Compound 9

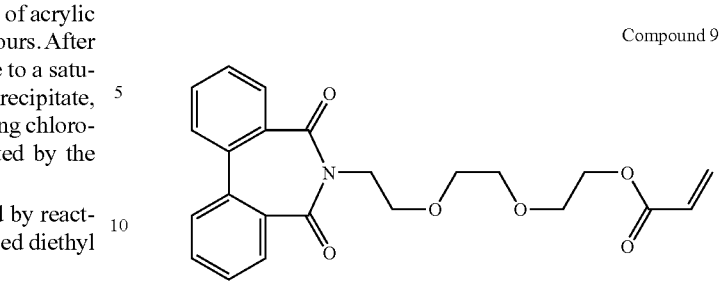

Example 10

As by-product of the synthesis in Example 7, a compound 10 was obtained. The structure was confirmed by NMR spectrum and IR spectrum:

Compound 10

Example 11

As by-product of the synthesis in Example 8, a compound 11 was obtained. The structure was confirmed by NMR spectrum and IR spectrum.

Compound 11

Example 12

As by-product of the synthesis in Example 9, a compound 12 was obtained. The structure was confirmed by NMR spectrum and IR spectrum:

Compound 12

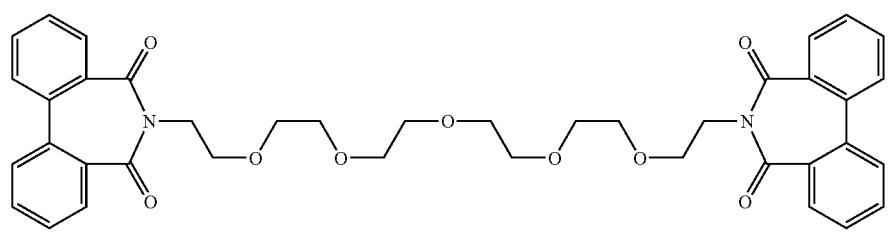

Example 13

A reaction was run in the same condition as in the Example 1 except that the amine as the starting material was altered to N,N-dimethylethylenediamine. Each raw material was supplied in the same number of moles as in Example 1. As the result, a compound 13 was obtained:

Compound 13

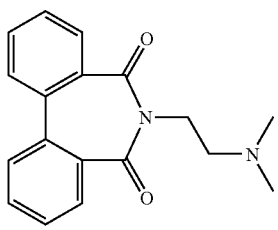

Example 14

A reaction was run in the same condition as in the Example 1 except that the amine as the starting material was altered to N,N-dimethylethylenediamine. Each raw material was supplied in the same number of moles as in Example 1. In the reaction, a compound 14 wherein a hydroxyl group in the end and a secondary amino group in the molecular chain were acetylated by acetic anhydride was quantitatively obtained since an amine having hydroxyl groups in the ends and a secondary amino group in the molecular chain was used:

Compound 14

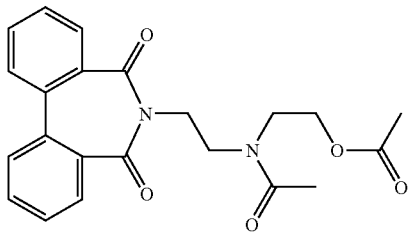

Example 15

(1) Synthesis of 4,4'-dinitrodiphenic Acid

A 500 ml eggplant-shape flask was charged with 4.84 g (20 mmol) of diphenic acid and 150 ml of concentrated sulfuric acid and cooled in an ice bath while stirring. Thereto, 5 ml of concentrated sulfuric acid was added dropwise slowly and carefully to keep temperature of the reaction solution 5° C. or less. After the dropping, the reaction solution was cooled in an ice bath for 2 hours and taken to ambient temperature to be stirred for 20 hours. After the reaction, 1 L of ice water was poured in the reaction solution and the precipitate was filtered. The filtrate was dissolved in 60 ml of ethanol while heating in a hot-water bath, and therein, 200 ml of distilled water was gradually added while heating to re-crystallize. After leaving in ambient temperature, the deposited crystal was filtered, thus, 6.37 g of 4,4'-dinitrodiphenic acid was obtained.

(2) Synthesis of a Compound 15

A 100 ml eggplant-shape flask was charged with 3.32 g (10 mmol) of 4,4'-dinitrodiphenic acid and 50 ml of acetic anhydride and stirred at 120° C. for 3 hours. Acetic anhydride was removed by a rotary evaporator. Then, dried DMF was added and stirred. Thereto, 0.75 g (10 mmol) of 2-methoxyethylamine was added and stirred at ambient temperature for 4 hours, and then, 30 ml of acetic anhydride was added and stirred at 120° C. for 5 hours. Then, DMF, acetic anhydride and the like were removed by a rotary evaporator. The sample was dissolved to DMF in an appropriate concentration, dropped in distilled water, and re-precipitated to be refined. After that, purification was performed by column chromatography using chloroform, and thus obtained a compound 15 represented by the following formula:

Compound 15

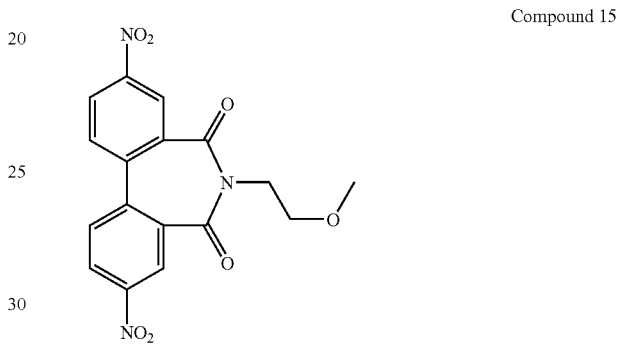

Comparative Example 1

Tetrahydrophthalic anhydride and 2-aminoehtanol were reacted in the same manner as disclosed in International Publication No. WO98/58912 to obtain a comparative compound 1:

Comparative compound 1

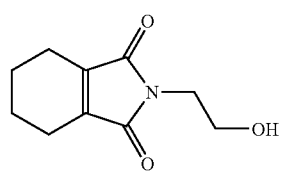

Comparative Compound 2

10.0 g (40 mmol) of the comparative compound 1 and 5.4 g (44 mmol) of 4-dimethylaminopyridine were poured into a 1 L three-neck flask. A calcium chloride pipe was attached to the center opening and the remainder two openings were sealed with a Silicon W Cap (trademark; manufactured by ASONE CORPORATION). 500 ml of tetrahydrofuran (THF) which had been dehydrated in advance was poured into there by using a syringe, followed by stirring at ambient temperature. 4.0 g (44 mmol) of acrylic acid chloride was added dropwise to there, followed by stirring at ambient temperature for 10 hours. Thereafter, the reaction solution was treated with 1N HCl by using a separating funnel to transfer 4-dimethylaminopyridine to the water phase. After the water phase was separated from the oil phase, the oil phase was further treated using a saturated NaHCO₃ solution to transfer acrylic acid originated from unreacted acrylic acid chloride to the water phase, and the oil phase was separated from the water phase. The oil phase obtained in this manner was dehydrated using a proper dehydrator such as magnesium sulfate or the like, followed by filtration. The filtrate, from which a solvent was removed, was re-crystallized from a chloroform-ethyl acetate mixed solvent to obtain 10.3 g of a comparative compound 2 represented by the following formula:

Comparative compound 2

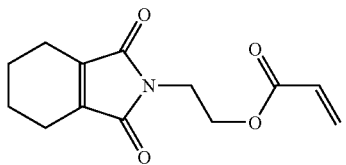

Comparative Example 3

A 1 L eggplant-shape flask was charged with 19.8 g (0.1 mol) of 1,8-naphthalic anhydride, 500 mL of N,N-dimethylformamide (hereinafter called DMF) and a catalytic amount of pyridine, and stirred. 8.3 g (0.11 mol) of 2-methoxyethylamine was added dropwise into there, which was then stirred at ambient temperature for 5 hours followed by stirring at 130° C. for 5 hours. DMF was partially distilled by a rotary evaporator to adjust concentration, followed by re-crystallizing by dropping to distilled water to obtain a comparative compound 3 represented by the following formula in an amount of 23.5 g (comparative compound 3):

Comparative compound 3

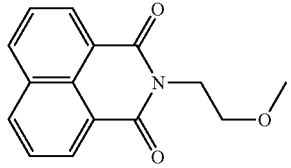

Evaluation (1) Evaluation of Ultraviolet Absorption

Figure 3:
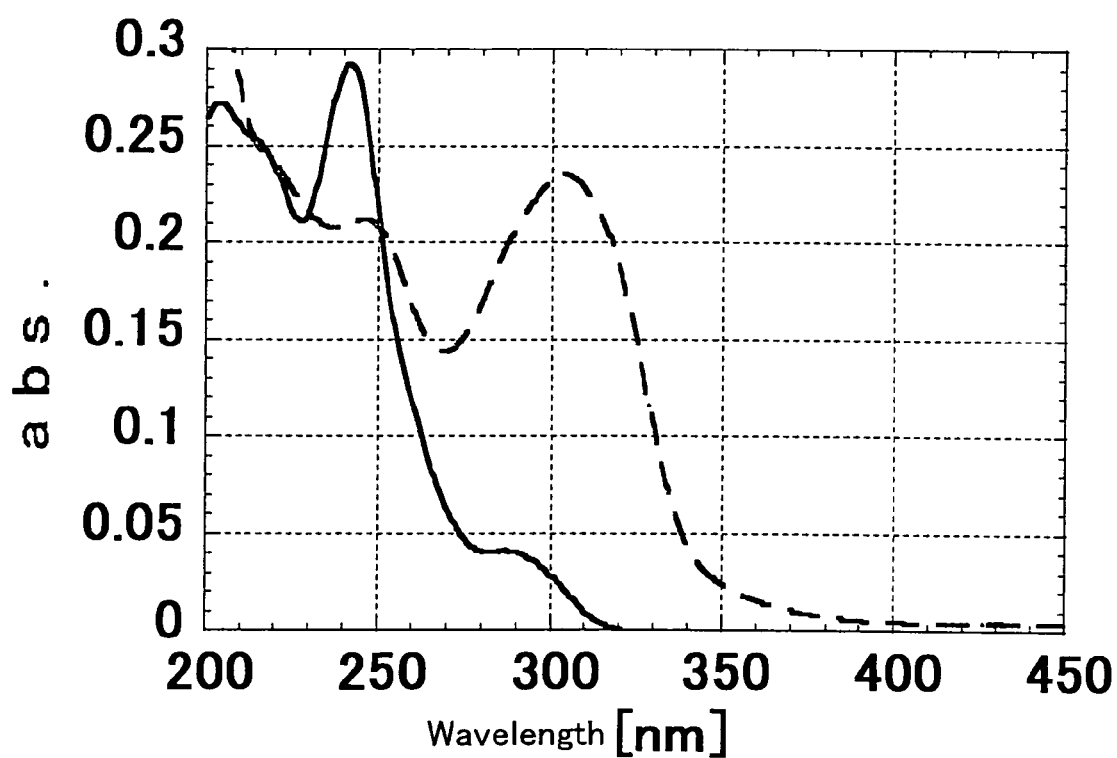
FIG. 3 is a graph showing the result of measurement of an ultraviolet absorption spectrum (compound 1)

Using an acetonitrile solution containing $1.0 \times 10^{-5}$ mol/L of each of the compounds 1 and 15, each ultraviolet absorption spectrum was measured. As the result, as shown in FIG. 3, it is confirmed that these compounds respectively have the maximum wavelength shifted by about 240 nm to have the bottom edge reached about 320 nm (in the graph, a solid line shows the compound 1 and a dotted line shows the compound 15).

Also, in the case of the compound B4 into which a nitro group was introduced, it has the absorption wavelength shifted to a longer wavelength side and has absorption at a wavelength of 365 nm which is the emitting wavelength of a high pressure mercury lamp which is a general exposure light source.

(2) Evaluation of Heat Resistance

Using a differential type differential thermal balance (product name: TG8120; manufactured by Rigaku Corporation), the 5% reduction in weight temperature of each of the compounds 1 to 15 was measured at a temperature rise rate of 10° C./min in a nitrogen atmosphere. As comparative examples, the comparative compounds 2 and 3 and a self-cleavage type photoradical generator Irgacure 907 (trademark; manufactured by Ciba Specialty Chemicals) were similarly measured.

The results of measurement are shown below. From these results, it was found out that each of the compounds 1 to 15 has a seven-membered ring imide structure-containing group, however, the 5% reduction in weight temperature thereof, except from example 13 having slightly lower 5% reduction in weight temperature, was higher than that of the comparative compound 2 having a five-membered ring imide structure, and further the compounds 1 to 15 have almost equal heat resistance to the comparative compound 3 having a six-membered ring imide structure. Also, it was clear that a compound a seven-membered ring imide structure-containing group has higher 5% reduction in weight temperature and heat resistance than a self-cleavage type photoradical generator Irgacure 907.

Among the compounds 1 to 15, the heat decomposition temperature of the compound 8 was specifically high. As for the compounds 7 and 8, even heated to 600° C. in a nitrogen atmosphere, carbide was left not decomposed completely. It is assumed that this is because the compounds 7 and 8 polymerized by heat in heating process since these compounds have acryloyl groups in the ends and decomposition was hard to occur.

As for the compound 15 which introduced a nitro group, the heat decomposition temperature improved by 50° C. or more in comparison with the compound 1 which is unsubstituted compound of the same side chain structure. It can be assumed that the improvement in heat resistance is due to introduction of a nitro group to.

TABLE 1

| Evaluation of heat resistance | |
|---|---|
| | 5% heat decomposition temperature (° C.) |
| Composition 1 | 224 |
| Composition 2 | 240 |
| Composition 3 | 260 |
| Composition 4 | 208 |
| Composition 5 | 213 |
| Composition 6 | 257 |
| Composition 7 | 233 |
| Composition 8 | 357 |
| Composition 9 | 295 |
| Composition 10 | 204 |
| Composition 11 | 240 |
| Composition 12 | 276 |
| Composition 13 | 177 |
| Composition 14 | 234 |
| Composition 15 | 280 |
| Comparative composition 2 | 184 |
| Comparative composition 3 | 229 |
| Irg907 | 207 |

(3) Evaluation 1 of Curability

Using a trifunctional acrylate (product name; M-305, manufactured by Toagosei Co., Ltd.) as polyfunctional monomers, the compounds 1 to 14, the comparative compounds 2 and 3 and a photoradical generator Irgacure 907

(product name; manufactured by Ciba Specialty Chemicals) were mixed with each polyfunctional monomer to prepare each THF solution of each photoradical generator.

The mixing was performed so that a ratio of the photoradical generator to the polyfunctional monomer is such that number of imide part of each of the compounds 1 to 14 and the comparative compounds 2 and 3 with respect to number of double bond of the polyfunctional monomer is 1/50 (number of imide part/number of polyfunctional monomer) or, in the case of Irgacure, number of the molecule with respect to number of double bond of the polyfunctional monomer is 1/50 (number of Irgacure 907/number of polyfunctional monomer).

trifunctional acrylate M305, does not generate odor during curing and could obtain significantly transparent coating layer. On the contrary, in the case of using Irgacure 907 which is a self-cleavage type, odor was generated during exposure and the obtained coating layer was colored as yellow.

Also, comparing compounds with same structures in end of the side chain, the tendency can be observed that the reaction rate improves when the ethylene glycol structure becomes longer though not completely.

Further, the compounds 10 to 12 which are dimmers showed relatively good sensitivity, which implied that high sensitivity, can be obtained without the presence of a hydrogen donor.

TABLE 2

Evaluation result 1 of curability

| Compound | Compatibility with M305 | Odor during exposure | Reaction rate [%] Exposure [mJ] 50 | 100 | 400 | Coloring in coating layer |
|---|---|---|---|---|---|---|
| 1 | ○ | No | 0.3 | 0.5 | 1.1 | Transparent |
| 2 | ○ | No | 0.1 | 0.2 | 1.2 | Transparent |
| 3 | ○ | No | 0.1 | 0.2 | 0.8 | Transparent |
| 4 | ○ | No | 0.2 | 0.4 | 0.9 | Transparent |
| 5 | ○ | No | 0.4 | 0.7 | 2.3 | Transparent |
| 6 | ○ | No | 3.2 | 5.4 | 14.2 | Transparent |
| 7 | ○ | No | 1.5 | 3.4 | 7.7 | Transparent |
| 8 | ○ | No | 5.0 | 7.3 | 21.4 | Transparent |
| 9 | ○ | No | 0.5 | 0.7 | 1.2 | Transparent |
| 10 | ○ | No | 4.0 | 6.8 | 17.4 | Transparent |
| 11 | ○ | No | 27.9 | 37.3 | 42.3 | Transparent |
| 12 | ○ | No | 11.0 | 15.2 | 24.8 | Transparent |
| 13 | ○ | No | 0.2 | 0.8 | 4.2 | Transparent |
| 14 | ○ | No | 1.0 | 2.0 | 6.4 | Transparent |
| Comparative compound 2 | ○ | No | 0.1 | 0.3 | 2.0 | Transparent |
| Comparative compound 3 | ○ | No | 1.0 | 2.5 | 26.6 | Transparent |
| Irg 907 | ○ | Yes | 34.8 | 40.8 | 50.6 | Yellow |

Hence, in the case of the compounds 10 to 12, which have two seven-membered ring imide structures in one molecule, the compounds 10 to 12 and the polyfunctional monomer were mixed so that the ratio of number of molecule of the compounds 10 to 12 with respect to that of polyfunctional group was 1/100.

Each solution was applied by spin coating to a glass substrate on which chromium was sputtered to obtain coating layers. Also, a layer without initiator component or comparative compounds and only containing trifunctional acrylate was formed as a blank.

A decrement of the peak at 810 cm$^{-1}$ was recorded with time by using an infrared spectrometer (product name: FTS6000; manufactured by BIO RAD) while exposing the above coating layer to ultraviolet rays, to confirm the degree of the disappearance of a double bond. The atmosphere around the sample during measurement was replaced with nitrogen. As the UV exposure apparatus, UV Spot Cure SP-III type (standard reflecting mirror type) manufactured by Ushio Inc. was used and as the UV lamp, USH-255BY (manufactured by Ushio Inc.) was used.

The compatibility with a trifunctional acrylate M305, odors during curing, a decrement of a double bond in relation to exposure amount (reaction rate) and coloring of the coating layer were observed. The results are shown in Table 2. As the result, a compound having a seven-membered ring imide structure-containing group was high in compatibility with (4) Evaluation 2 of Curability In order to confirm whether or not the seven-membered ring imide structure-containing group was a hydrogen-drawing type radical generator, triethanolamine was added to THF solutions containing each of the compositions 1 to 14 used in the aforementioned Evaluation 1 of curability and trifunctional acrylate M305, coating layers were formed in the same manner as in the aforementioned Evaluation 1 of curability, and evaluated similarly. As comparative examples, each of the comparative compounds 1 and 3 was used. The results are shown in Table 3.

As shown in the above Table 2 (Evaluation 1 of curability), the reaction rate does not increase by light radiation in the case of not adding a hydrogen donor. It can be assumed that this is because UV absorption of the compound having a seven-membered ring imide structure-containing group is not largely overlapped on the emitting wavelength of a high-pressure mercury lamp which is a irradiating light source.

On the contrary, it was confirmed that the reaction rate was dramatically improved by addition of triethanolamine to the same solution as a hydrogen donor. From this result, it was assumed that a seven-membered ring imide structure-containing group is a hydrogen-drawing type photoradical generator. Further, sensitivity can be improved by compounding a hydrogen-donating group represented by amine in a photosensitive resin composition of the present invention.

TABLE 3

Evaluation result 2 of curability

| Compound | Compatibility with M305 | Odor during exposure | Reaction rate [%] Exposure [mJ] | | | Coloring in coating layer |
|---|---|---|---|---|---|---|
| | | | 50 | 100 | 400 | |
| 1 | ○ | No | 17.3 | 23.6 | 36.6 | Transparent |
| 2 | ○ | No | 23.7 | 29.4 | 41.1 | Transparent |
| 3 | ○ | No | 26.8 | 32.7 | 43.7 | Transparent |
| 4 | ○ | No | 22.0 | 28.2 | 40.0 | Transparent |
| 5 | ○ | No | 23.8 | 29.2 | 41.0 | Transparent |
| 6 | ○ | No | 33.1 | 37.9 | 47.9 | Transparent |
| 7 | ○ | No | 25.3 | 30.1 | 41.3 | Transparent |
| 8 | ○ | No | 36.2 | 41.4 | 51.4 | Transparent |
| 9 | ○ | No | 13.8 | 19.9 | 34.4 | Transparent |
| 10 | ○ | No | 30.8 | 40.7 | 45.9 | Transparent |
| 11 | ○ | No | 18.0 | 21.3 | 29.4 | Transparent |
| 12 | ○ | No | 25.2 | 30.7 | 40.6 | Transparent |
| 13 | ○ | No | 11.0 | 15.2 | 24.8 | Transparent |
| 14 | ○ | No | 16.8 | 20.9 | 30.5 | Transparent |
| Comparative compound 2 | ○ | No | 1.3 | 2.0 | 8.6 | Transparent |
| Comparative compound 3 | ○ | No | 3.3 | 5.4 | 11.1 | Transparent |

(4) Solubility Test

As for the compound 1 and the comparative compound 3, a solubility test was performed respectively. Each sample was added to each solvent or monomer so as to be 0.5 mol/L at 20° C. After radiating ultrasonic wave for 3 hours, one with a precipitate was concluded as "○" and one without a precipitate was concluded as "x". As shown in the Table below, the compound 1 having a seven-membered ring imide structure is superior in solubility to the comparative compound 3 having naphthalimide structure.

TABLE 4

Solubility test result

| | Compound 1 | Comparative compound 3 |
|---|---|---|
| Chloroform | ○ | ○ |
| Acetone | ○ | ○ |
| Dimethylformamide | ○ | ○ |
| Tetrahydrofuran | ○ | ○ |
| Ethyl acetate | ○ | x |
| Propylene glycol monoethyl ether acetate | ○ | x |
| Ethyl lactate | ○ | x |
| Methyl acrylate | ○ | x |
| Pentaerythritol triacrylate (M305) | ○ | x |

(6) Evaluation of Transparency

Using a trifunctional acrylate (product name; M305, manufactured by Toagosei Co., Ltd.) as polyfunctional monomers, each of the compound 1, a combination of the compound 1 and triethanolamine of the same number of mol and a photoradical generator Irgacure 907 (Irg907) were mixed to prepare each THF solution in the same ratio as the Evaluation of curability. Each solution was applied by spin coating to a glass substrate and heated on a 50° C. hot plate for one minute. Then, the substrate was exposed to light from a high pressure mercury lamp at an intensity of 2,000 mJ/cm$^2$ based on h-rays by using a hand-operated exposure apparatus (MA-1200, manufactured by Dainippon Screen Mfg. Co., Ltd.), to obtain a coating layer having a thickness of 4.2±0.05 μm. The transmittance of each coating layer was measured by a spectrometer (UV-2550 (PC)S GLP; manufactured by Shimadzu Corporation).

Figure 4:
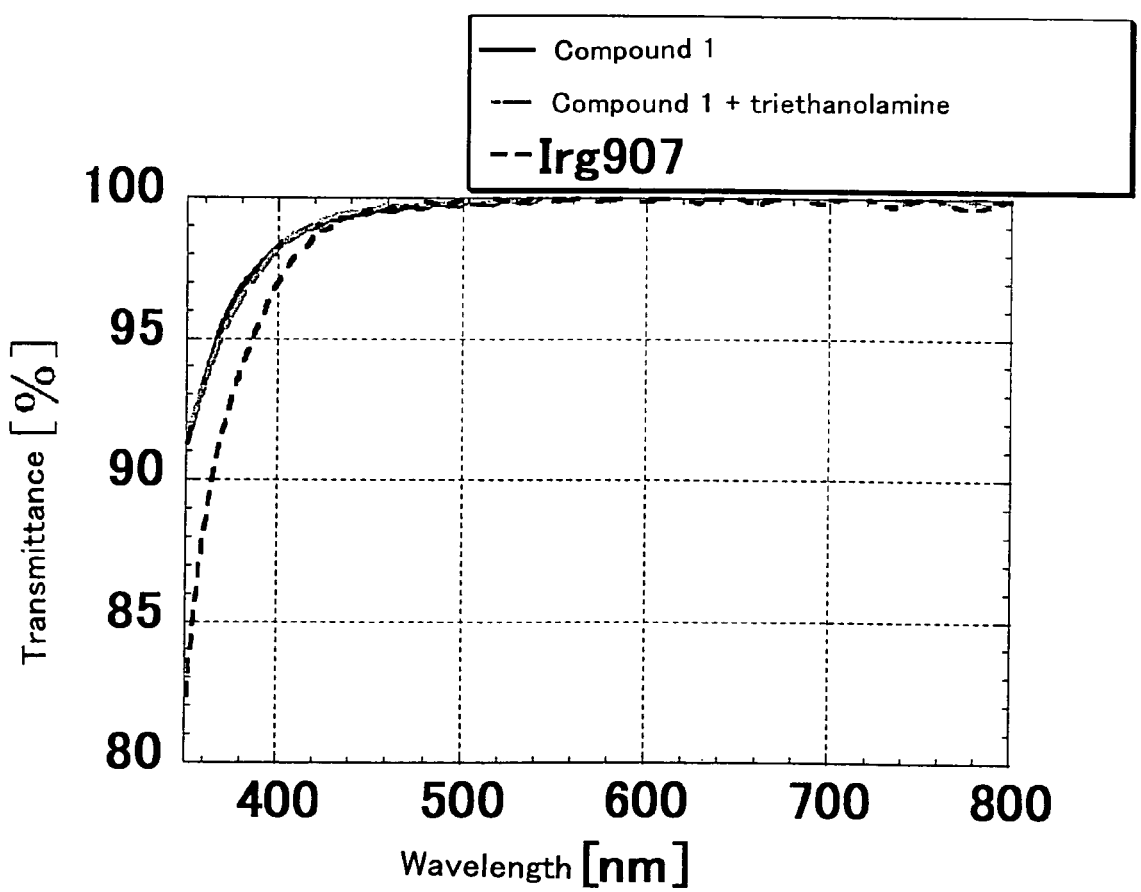
FIG. 4 is a graph showing the results of measurement of a transmittance (compound 1, compound 1+triethanolamine, Irg907).

The measured results are shown in FIG. 4. The cured layer using the compound 1 was high in transmittance with respect to the light of 410 nm or less and has good transparency compared to the cured layer using Irg907. Similarly, the coating layer wherein amine was added to the compound 1 was almost same in transmittance as in the case of only the compound 1 and good in transmittance.

What is claimed is:

1. A photoradical generator comprising a compound (a) having a seven-membered ring imide structure-containing group represented by the following formula (2):

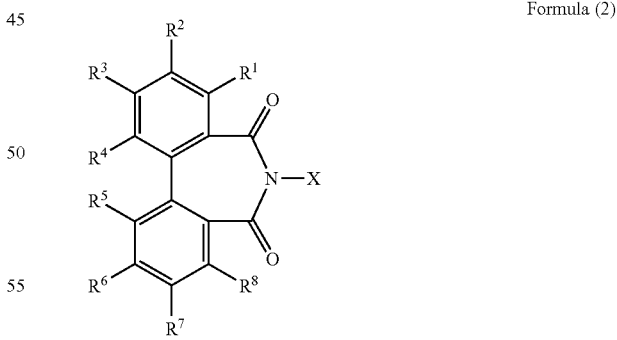

Formula (2)

wherein, $R^1$, $R^2$, $R^3$, $R^4$, $R^5$, $R^6$, $R^7$ and $R^8$ respectively represent a hydrogen atom or a substituent and may be a cyclic structure in which they are bonded to each other; "X" represents a monovalent chemical structure having a part of a non-aromatic skeleton containing a hydrocarbon skeleton directly bonded to "N" of the seven-membered ring imide structure-containing group and a part containing a hydrogen-donating atom; when groups selected from the group consisting of $R^1$, $R^2$, $R^3$, $R^4$, $R^5$, $R^6$, $R^7$ and $R^8$ are bonded to each other to have a cyclic structure, the cyclic structure is a structure that can keep a twist of two aromatic rings contained in a biphenyl structure contained in said formula.

2. A photoradical generator according to claim 1, wherein $R^1$, $R^2$, $R^3$, $R^4$, $R^5$, $R^6$, $R^7$ and $R^8$ in the formula (2) respectively represent a hydrogen atom, a halogen atom, a hydroxyl group, a mercapto group, an amino group, a cyano group, a silyl group, a silanol group, an alkoxy group, a nitro group, a carboxyl group, an acetyl group, an acetoxy group, a sulfone group or an organic group which may have a substituent or a cyclic structure in which they are bonded to each other.

3. A photoradical generator according to claim 1, wherein, in the compound (a) represented by the formula (2), "X" represents a structure having one or more ethylenic unsaturated bonds.

4. A photoradical generator according to claim 1, wherein, in the compound (a) represented by the formula (2), "X" represents a structure further having one or more seven-membered ring imide structure-containing groups represented by the following formula (1):

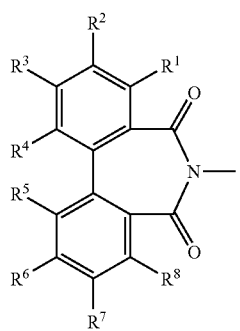

Formula (1)

wherein symbols in the formula (1) are identical to those in the formula (2).

5. A photoradical generator according to claim 1, wherein a value obtained by dividing a molecular weight of the compound (a) by number of seven-membered ring imide structure-containing group in one molecule of the compound (a) is 2,000 or less.

6. A photoradical generator according to claim 1, wherein a 5 % reduction in weight temperature is 50° C. or more.

7. A photosensitive resin composition comprising a compound (a) having a seven-membered ring imide structure-containing group represented by the formula 2 and a compound (b) having an ethylenic unsaturated group:

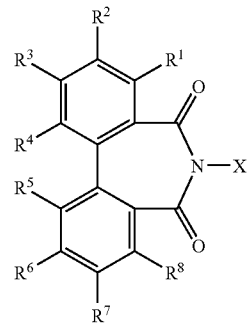

Formula (2)

wherein, $R^1$, $R^2$, $R^3$, $R^4$, $R^5$, $R^6$, $R^7$ and $R^8$ respectively represent a hydrogen atom or a substituent. and may be a cyclic structure in which they are bonded to each other: "X" represents a monovalent chemical structure having a part of a non-aromatic skeleton containing a hydrocarbon skeleton directly bonded to "N" of the seven-membered ring imide structure-containing group and a part containing a hydrogen-donating atom: when groups selected from the group consisting of $R^1$, $R^2$, $R^3$, $R^4$, $R^5$, $R^6$, $R^7$ and $R^8$ are bonded to each other to have a cyclic structure, the cyclic structure is a structure that can keep a twist of two aromatic rings contained in a biphenyl structure contained in said formula.

8. A photosensitive resin composition according to claim 7, wherein the photosensitive resin composition further contains at least a component selected from the group consisting of a hydrogen donor, a curable reactive compound except for the compound (b), a radical generator except for the compound (a), and a binder resin having a weight average molecular weight of 3,000 or more.

9. A photosensitive resin composition according to claim 7, wherein the photosensitive resin composition is used as a pattern-forming material.

10. A photosensitive resin composition according to claim 7, wherein the photosensitive resin composition is used as a paint or a printing ink, or as a material to form a color filter, electronic parts, a layer insulation film, a wire cover film, and optical member, an optical circuit, optical circuit parts, an antireflection film, a hologram or building material.

11. An article selected from the group consisting of a printed product, a color filter, electronic parts, a layer insulation film, a wire cover film, an optical member, an optical circuit, optical circuit parts, an antireflection film, a hologram and a building material at least a part which is formed of a cured product of the photosensitive resin composition according to claim 7.

* * * * *